US009693891B2

(12) United States Patent
MacIntyre-Ellis et al.

(10) Patent No.: US 9,693,891 B2
(45) Date of Patent: Jul. 4, 2017

(54) COST-EFFECTIVE SYSTEMS AND METHODS FOR ENHANCED NORMOTHERMIA

(71) Applicant: Pintler Medical LLC, Seattle, WA (US)

(72) Inventors: Maribeth MacIntyre-Ellis, Seattle, WA (US); Kent D Ellis, Seattle, WA (US); Thomas Shurr, Norton, OH (US)

(73) Assignee: Pintler Medical, LLC, Seattle, WA (US)

( * ) Notice: Subject to any disclaimer, the term of this patent is extended or adjusted under 35 U.S.C. 154(b) by 0 days.

(21) Appl. No.: 14/544,138

(22) Filed: Dec. 1, 2014

(65) Prior Publication Data
US 2015/0088233 A1    Mar. 26, 2015

Related U.S. Application Data

(63) Continuation-in-part of application No. 13/610,695, filed on Sep. 11, 2012, now abandoned.

(51) Int. Cl.
| *A61N 1/00* | (2006.01) |
| *A61F 7/08* | (2006.01) |
| *A61F 7/00* | (2006.01) |
| *A61B 18/16* | (2006.01) |
| *A61B 18/00* | (2006.01) |

(52) U.S. Cl.
CPC .............. *A61F 7/08* (2013.01); *A61B 18/16* (2013.01); *A61F 7/007* (2013.01); *A61B 2018/00797* (2013.01); *A61B 2018/00815* (2013.01); *A61B 2018/167* (2013.01); *A61F 2007/0071* (2013.01); *A61F 2007/0086* (2013.01); *A61F 2007/0094* (2013.01)

(58) Field of Classification Search
USPC ......................................................... 607/104
See application file for complete search history.

(56) References Cited

U.S. PATENT DOCUMENTS

| 7,908,812 B2 | 3/2011 | Eberle, III |
| 7,926,226 B2 | 4/2011 | Pope |
| 8,091,500 B2 | 1/2012 | Stroud |
| 8,256,614 B1 | 9/2012 | Wadsworth, Sr. |
| 8,272,190 B2 | 9/2012 | Schiffmann et al. |
| 8,291,647 B2 | 10/2012 | Esposito |
| 8,322,097 B2 | 12/2012 | Schiffmann et al. |
| 8,371,556 B2 | 2/2013 | Price |
| 8,499,505 B2 | 8/2013 | Pulte |
| 8,516,777 B2 | 8/2013 | Schiffmann et al. |
| 8,714,887 B2 | 5/2014 | Tipps et al. |
| 8,739,489 B2 | 6/2014 | Weber et al. |
| 2006/0076545 A1 | 4/2006 | Reynders et al. |
| 2010/0087900 A1* | 4/2010 | Flint ........................ A61F 7/12 607/104 |
| 2012/0328823 A1 | 12/2012 | Monteer |
| 2013/0111840 A1 | 5/2013 | Bordener |

OTHER PUBLICATIONS http://hotdog-usa.com/images/PDFs/US/M103-HotDogTechnicalBrochure.pdf.

* cited by examiner

*Primary Examiner* — Nicole F Lavert

(57) ABSTRACT

Structures and protocols are presented for supporting a medical or veterinary patient with therapeutically significant normothermia and other practical advantages.

13 Claims, 15 Drawing Sheets

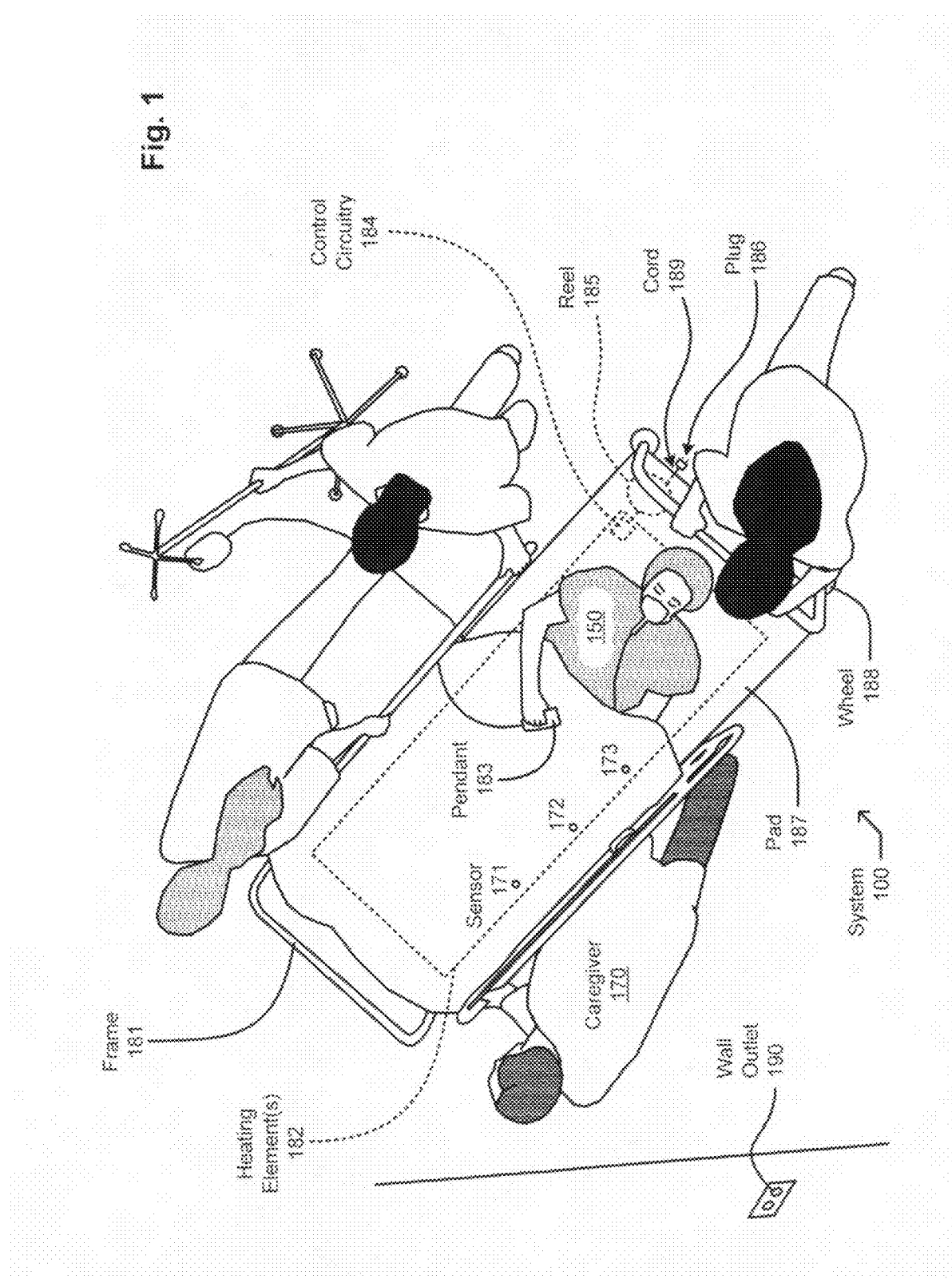

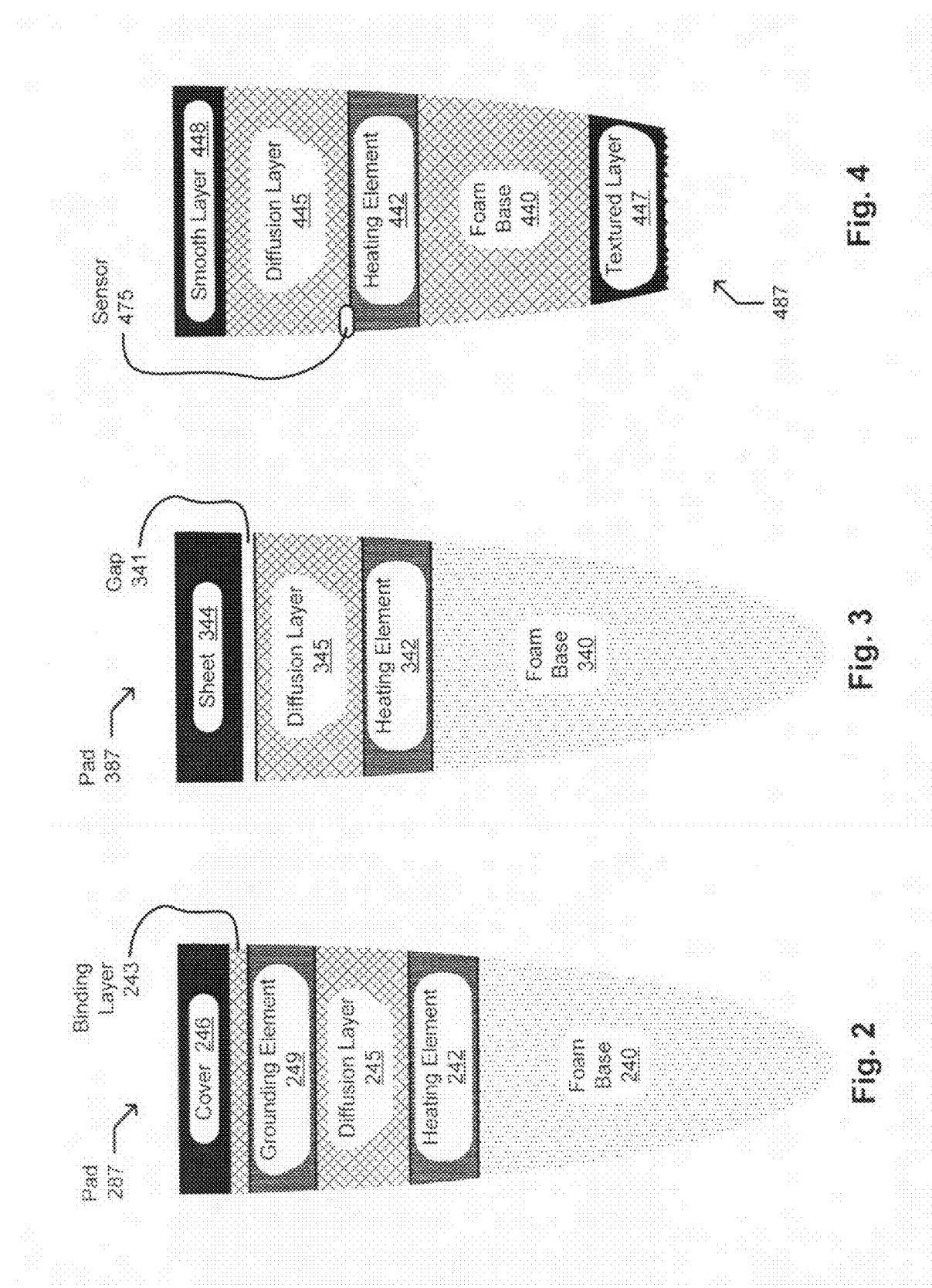

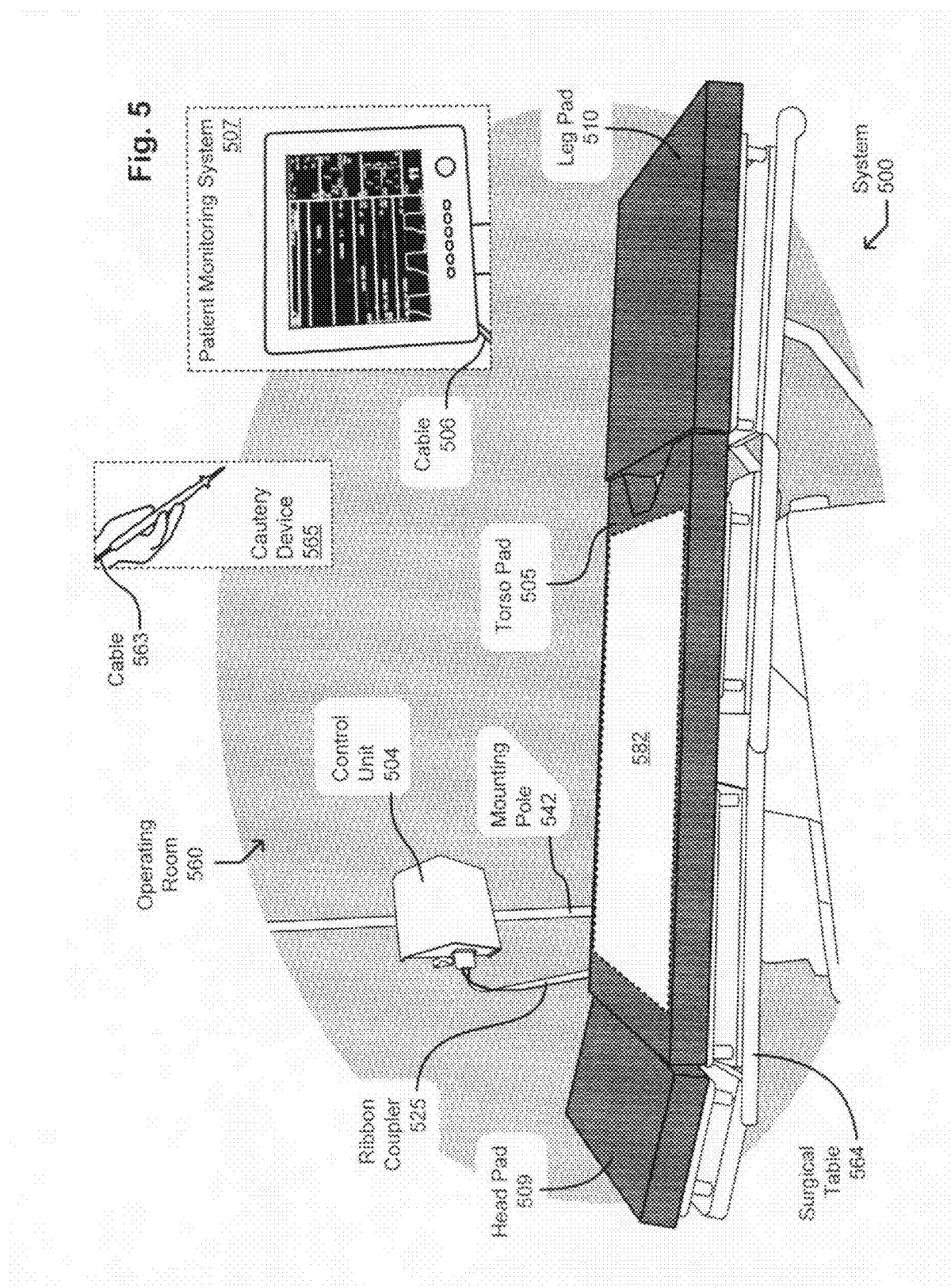

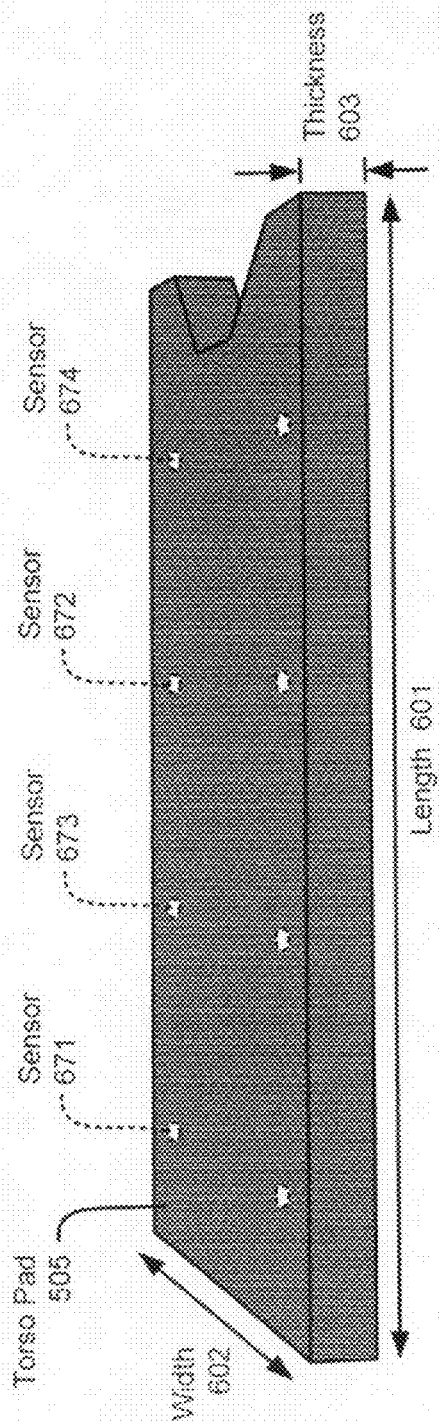
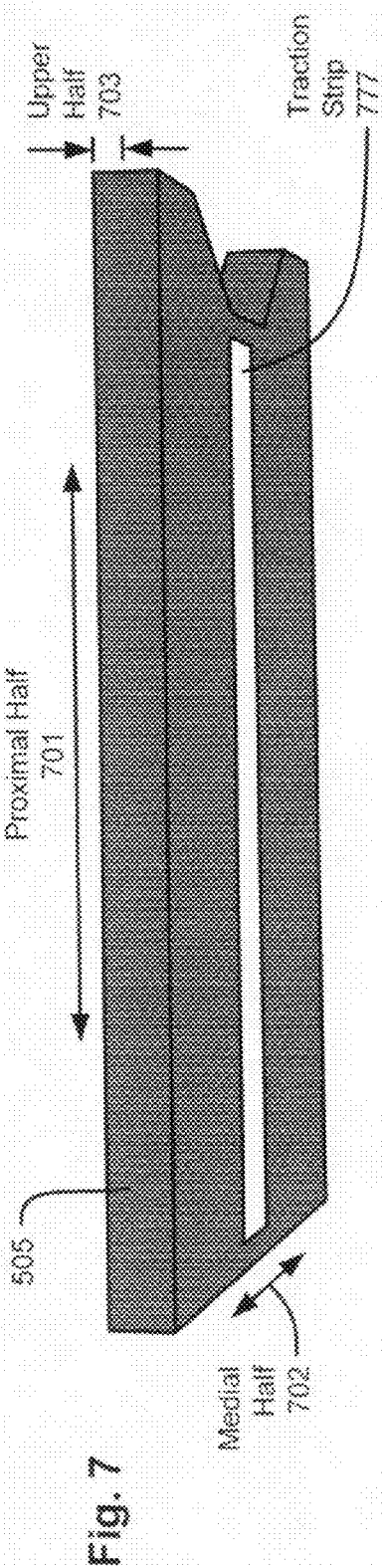
Fig. 6
Fig. 7

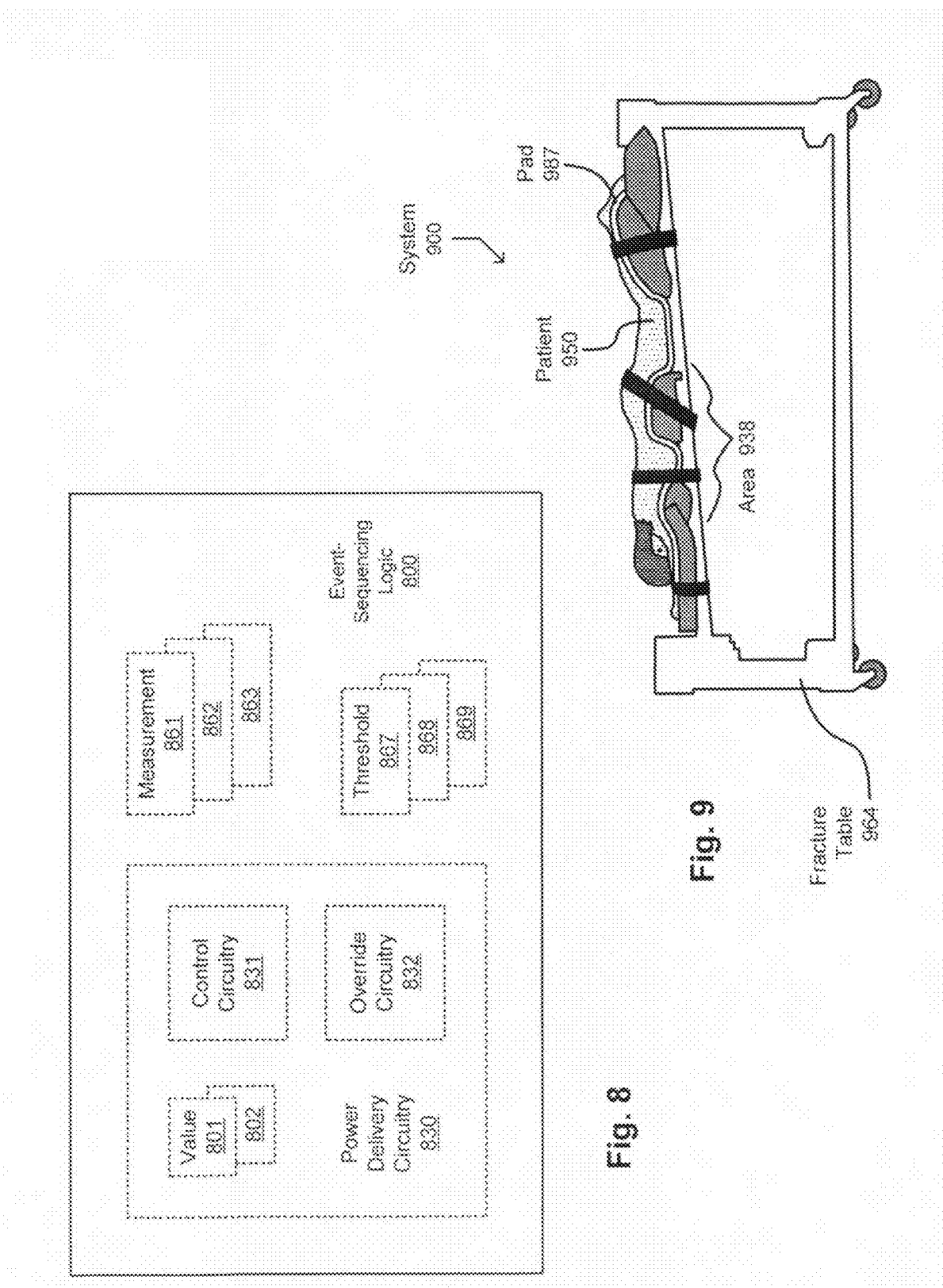

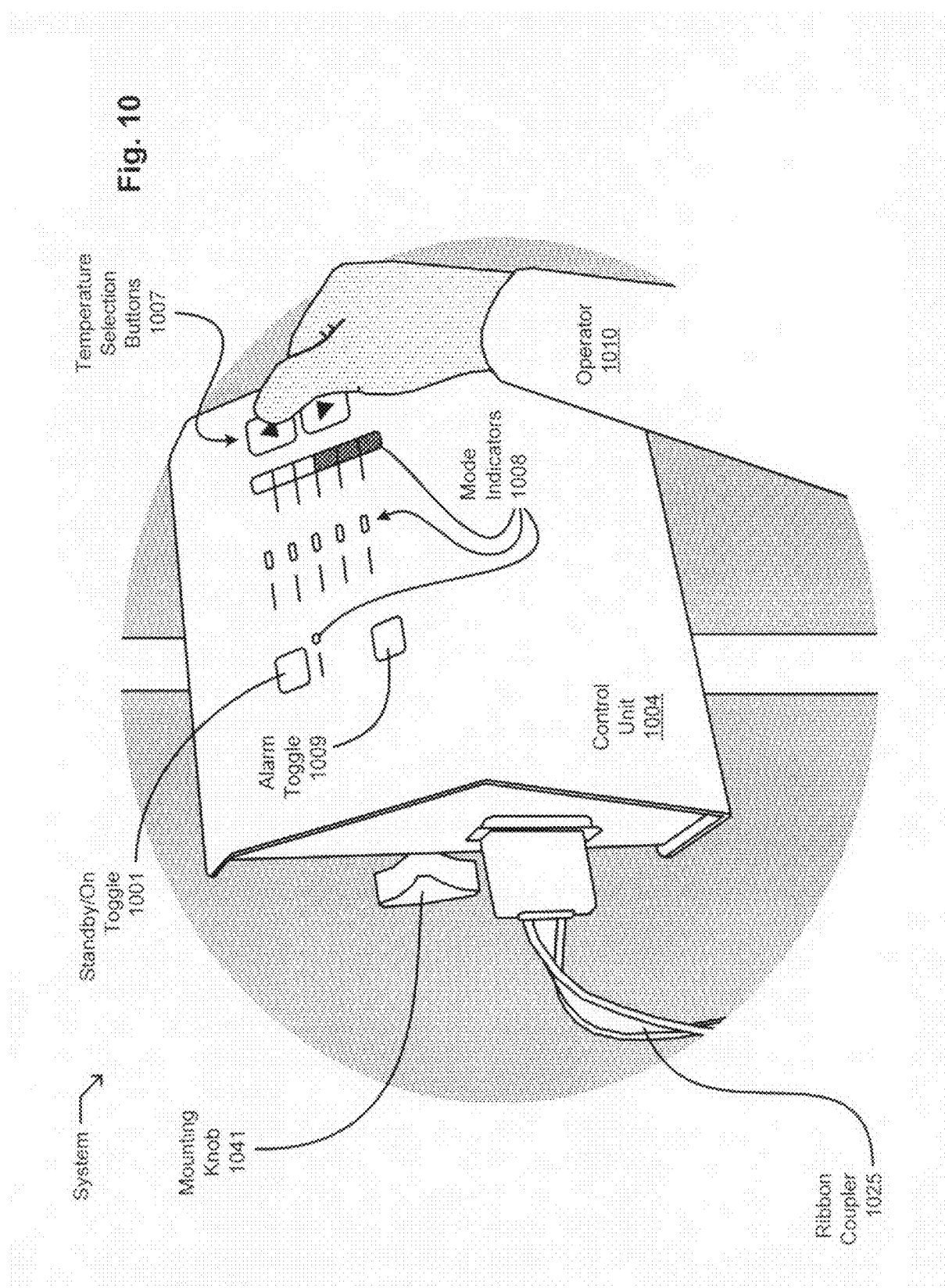

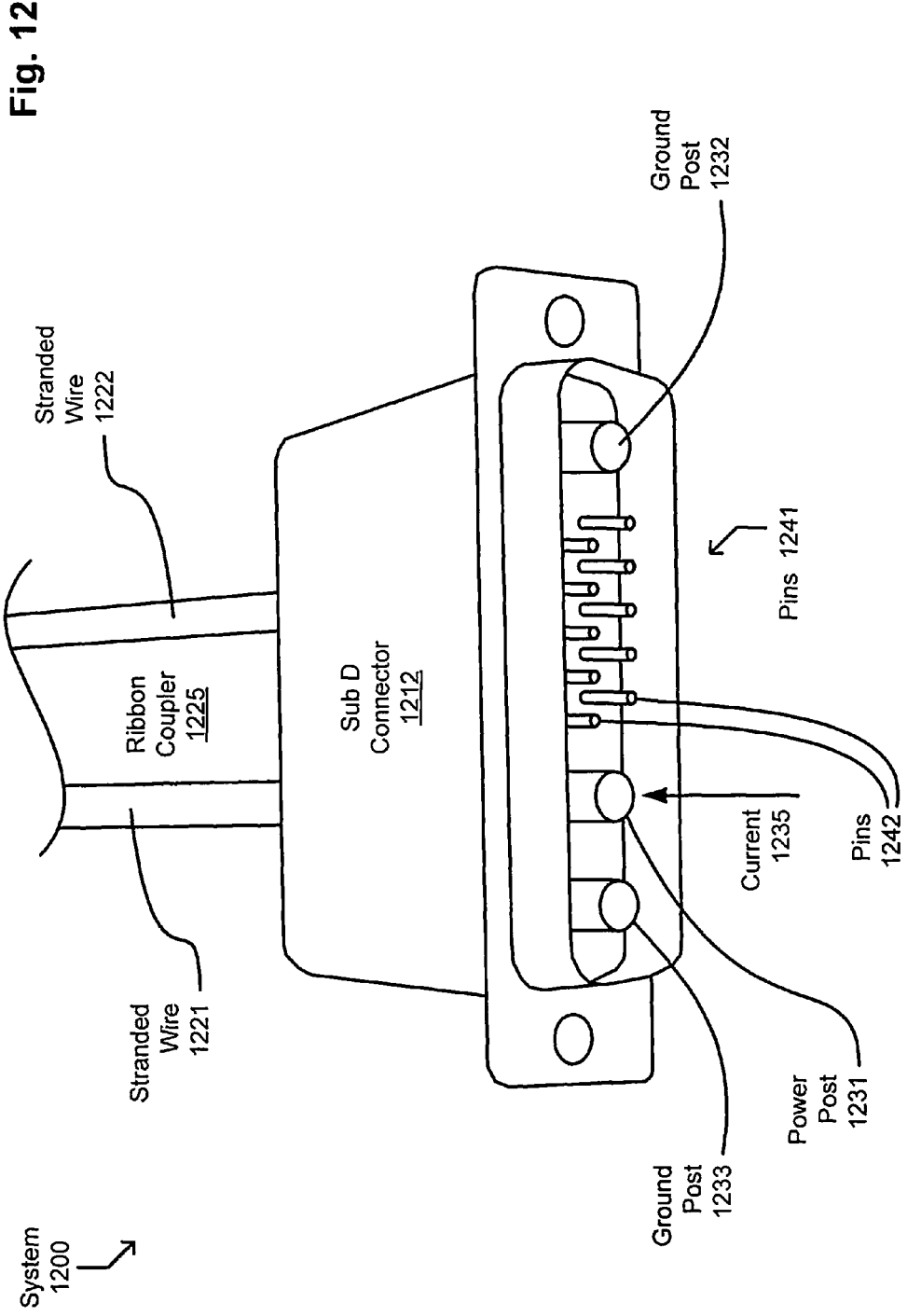

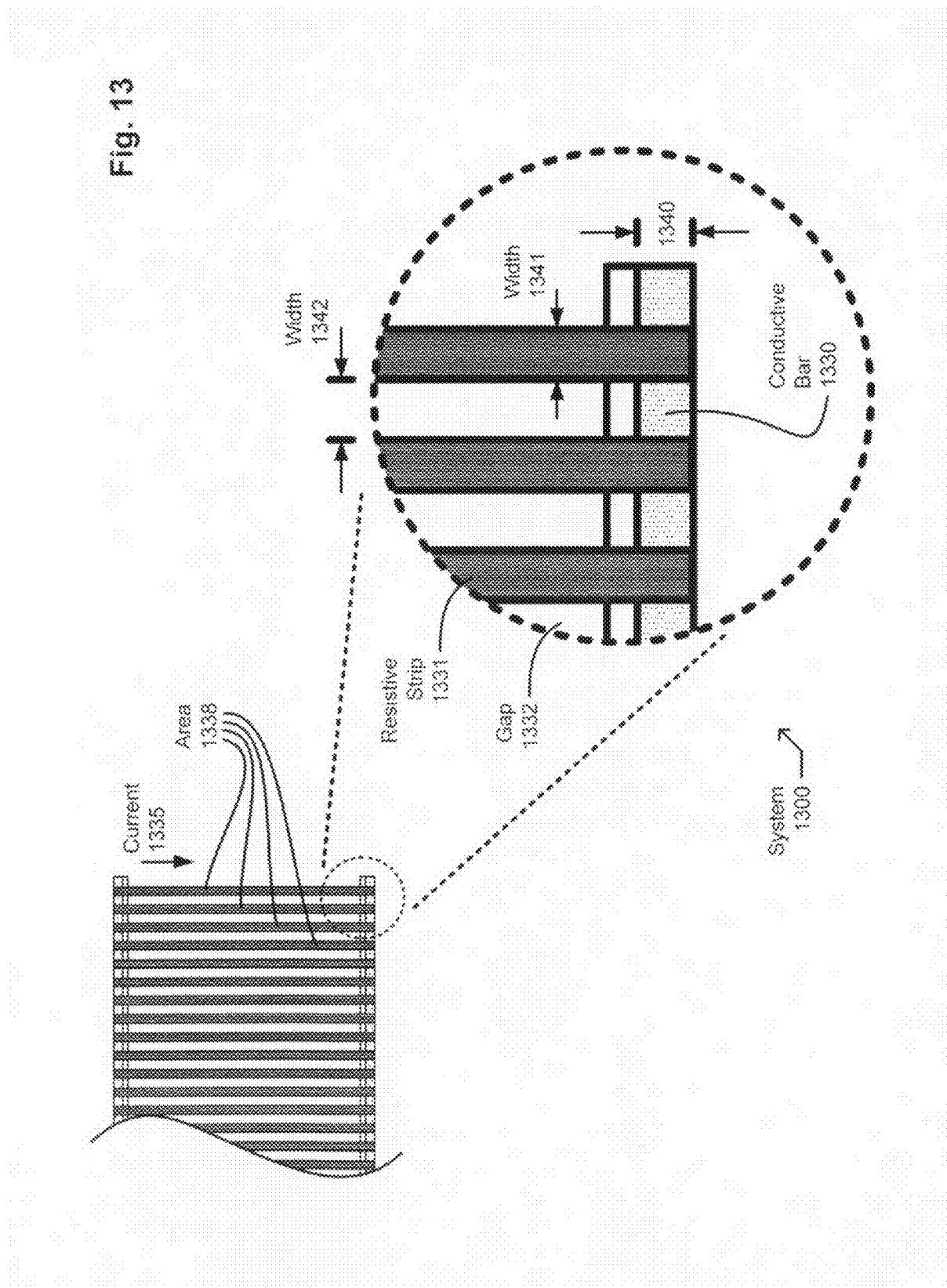

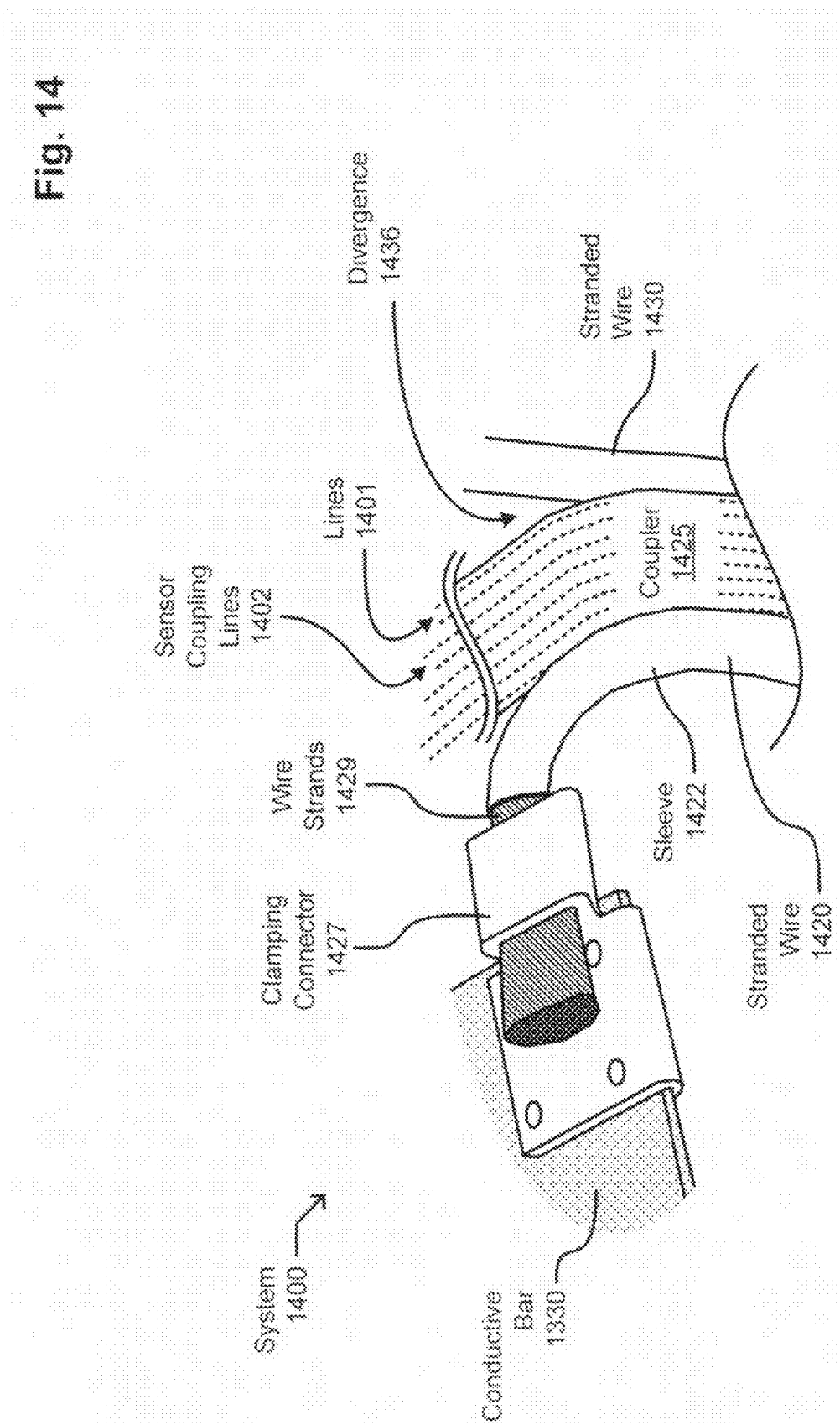

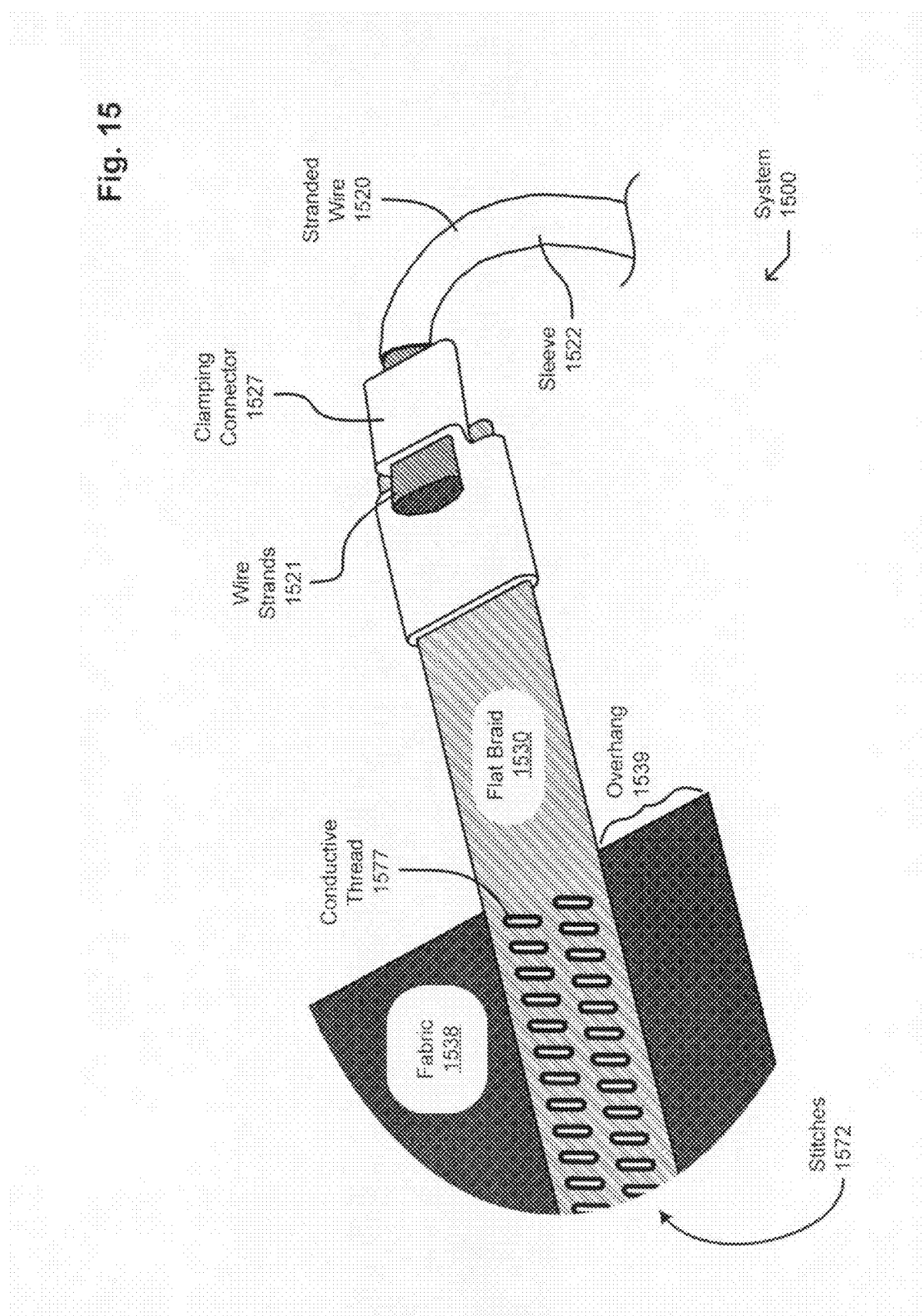

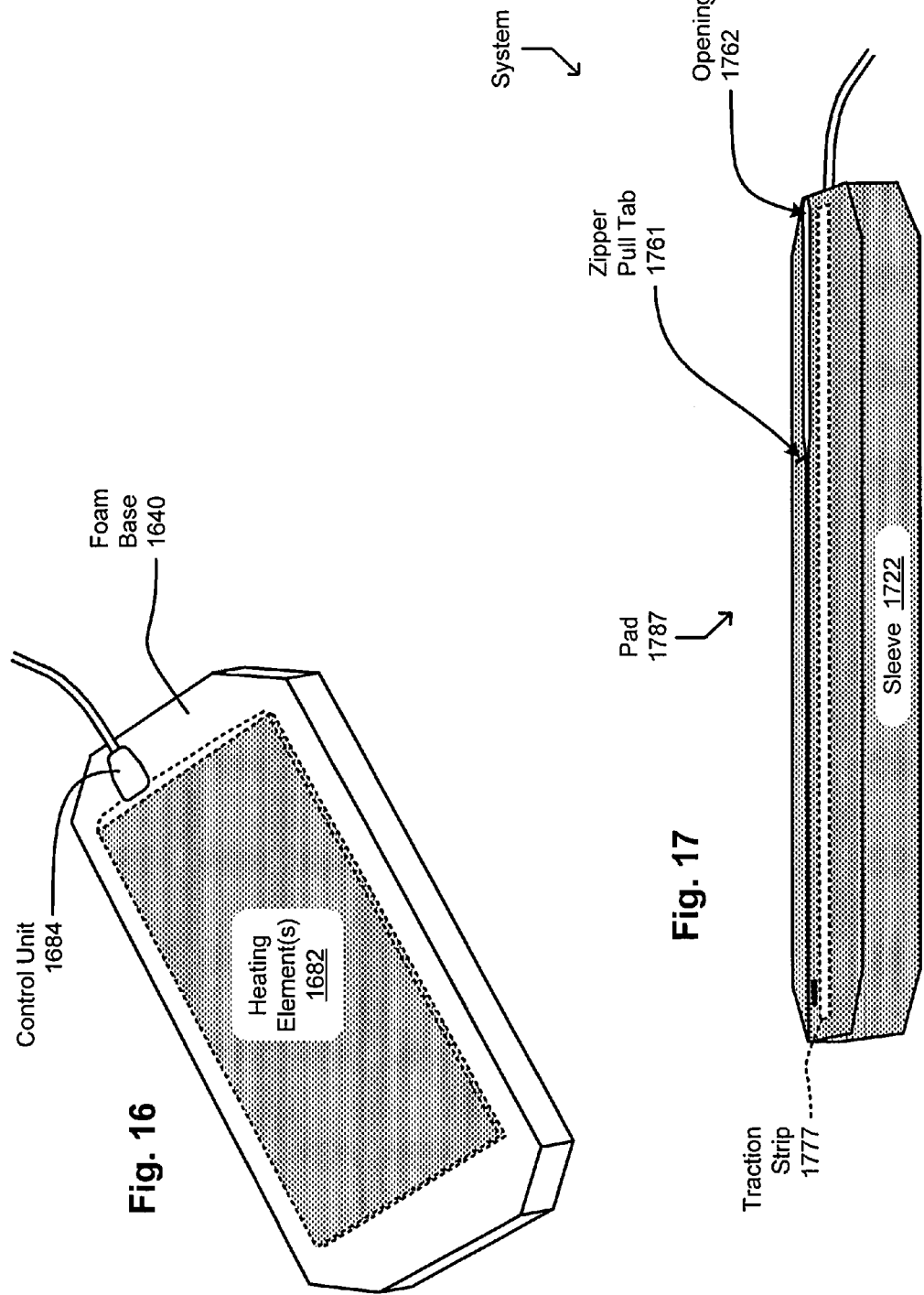

COST-EFFECTIVE SYSTEMS AND METHODS FOR ENHANCED NORMOTHERMIA

RELATED APPLICATIONS

The present application claims benefit of priority of U.S. patent application Ser. No. 13/610,695 (filed 11 Sep. 2012) or is an application of which a currently co-pending application is entitled to the benefit of the filing date.

SUMMARY

Various novel normothermia implementation systems and methods are presented, each effective for enhancing outcomes of medical or veterinary procedures without undue burden upon caregivers. As used herein, the term "therapeutically significant" normothermia is used to describe an implementation effective for delivering more than 10 watts thermally conducted to a patient. This rate of heat delivery has been correlated with improving a patient's likelihood of surviving a life-threatening emergency significantly (by 0.2% or more, e.g.), especially when delivered in the manner described herein (via large form heating element configurations in a heat conduction structure, e.g.).

In one or more various aspects, for example, a normothermia implementation method includes but is not limited to providing a heat diffusion layer, a first heating element at the heat diffusion layer, one or more thermal control sensors configured to obtain a first temperature measurement at the heat diffusion layer, one or more thermal safety sensors configured to obtain a second temperature measurement at the heat diffusion layer, and override circuitry operably coupled to the first heating element at the heat diffusion layer; causing interface circuitry to indicate a selected one from a plurality of modes that includes at least a first operator-selectable mode in which at least one thermal safety sensor of the one or more thermal safety sensors at the heat diffusion layer is powered but in which the first heating element at the heat diffusion layer is unpowered and that includes a second operator-selectable mode in which the one thermal safety sensor at the heat diffusion layer is powered and in which the first heating element at the heat diffusion layer is actively controlled; and causing primary control circuitry configured to control the first heating element at the heat diffusion layer as an automatic and conditional response to the one thermal control sensor at the heat diffusion layer indicating a first temperature measurement differing from a target value if the second operator-selectable mode in which the one thermal safety sensor at the heat diffusion layer is powered and in which the first heating element at the heat diffusion layer is actively controlled is the selected one of the plurality unless the override circuitry deactivates the first heating element at the heat diffusion layer as an automatic and conditional response to the one thermal safety sensor at the heat diffusion layer indicating the second temperature measurement exceeding a thermal safety threshold, whether or not the primary control circuitry controls the first heating element at the heat diffusion layer as the automatic and conditional response to the first temperature sensor at the heat diffusion layer indicating the first temperature measurement differing from the target value being at least partly based on whether or not the first operator-selectable mode in which the one thermal safety sensor at the heat diffusion layer is powered but in which the first heating element at the heat diffusion layer is unpowered is the selected one of the plurality. In addition to the foregoing, other method aspects are described in the claims, drawings, and text forming a part of the disclosure set forth herein.

An embodiment provides a normothermia implementation system. In one variant, the normothermia implementation system includes but is not limited to a heat diffusion layer; a first heating element at the heat diffusion layer; one or more thermal control sensors configured to obtain a first temperature measurement at the heat diffusion layer; one or more thermal safety sensors configured to obtain a second temperature measurement at the heat diffusion layer; override circuitry operably coupled to the first heating element at the heat diffusion layer; interface circuitry configured to indicate a selected one from a plurality of modes that includes at least a first operator-selectable mode in which at least one thermal safety sensor of the one or more thermal safety sensors at the heat diffusion layer is powered but in which the first heating element at the heat diffusion layer is unpowered and that includes a second operator-selectable mode in which the one thermal safety sensor at the heat diffusion layer is powered and in which the first heating element at the heat diffusion layer is actively controlled; and primary control circuitry configured to control the first heating element at the heat diffusion layer as an automatic and conditional response to the one thermal control sensor at the heat diffusion layer indicating a first temperature measurement differing from a target value if the second operator-selectable mode in which the one thermal safety sensor at the heat diffusion layer is powered and in which the first heating element at the heat diffusion layer is actively controlled is the selected one of the plurality unless the override circuitry deactivates the first heating element at the heat diffusion layer as an automatic and conditional response to the one thermal safety sensor at the heat diffusion layer indicating the second temperature measurement exceeding a thermal safety threshold.

An embodiment provides a normothermia implementation method. In one variant, the normothermia implementation method includes but is not limited to providing a portable frame supporting one or more pads containing one or more heating elements having an active element area totaling more than one square foot adjacent a heat diffusion layer configured to support a patient; supporting by the portable frame a retractable cord including an electrical wall plug configured to engage a wall outlet; and causing control circuitry to decide whether or not to cause the one or more heating elements to implement therapeutically significant normothermia by thermal conduction to the patient by passing current from the retractable cord supported by the portable frame through the active element area totaling more than one square foot adjacent the heat diffusion layer configured to support the patient. In addition to the foregoing, other method aspects are described in the claims, drawings, and text forming a part of the disclosure set forth herein.

An embodiment provides a normothermia implementation system. In one variant, the normothermia implementation system includes but is not limited to a portable frame supporting one or more pads containing one or more heating elements having an active element area totaling more than one square foot adjacent a heat diffusion layer configured to support a patient; a retractable cord supported by the portable frame and including an electrical wall plug configured to engage a wall outlet; and control circuitry configured to decide whether or not to cause the one or more heating elements to implement therapeutically significant normothermia by thermal conduction to the patient by passing current from the retractable cord supported by the portable frame through the active element area totaling more than one square foot adjacent the heat diffusion layer configured to support the patient.

An embodiment provides a normothermia implementation method. In one variant, the normothermia implementation method includes but is not limited to assembling one or more pads having an active element area totaling more than one square foot adjacent a heat diffusion layer configured to support a patient; and causing primary control circuitry to implement a decision whether or not to cause the one or more heating elements to administer a therapeutically significant amount of power as thermal energy by passing current through the active element area totaling more than one square foot partly based on one or more thermal control sensors at the heat diffusion layer and partly based on an indication of a user preference and partly based on a compression-sensitive element indicating the patient being supported by the heat diffusion layer. In addition to the foregoing, other method aspects are described in the claims, drawings, and text forming a part of the disclosure set forth herein.

An embodiment provides a normothermia implementation system. In one variant, the normothermia implementation system includes but is not limited to one or more pads having an active element area totaling more than one square foot adjacent a heat diffusion layer configured to support a patient; and primary control circuitry configured to implement a decision whether or not to cause the one or more heating elements to administer a therapeutically significant amount of power as thermal energy by passing current through the active element area totaling more than one square foot partly based on one or more thermal control sensors at the heat diffusion layer and partly based on an indication of a user preference and partly based on a compression-sensitive element indicating the patient being supported by the heat diffusion layer.

An embodiment provides a normothermia implementation method. In one variant, the normothermia implementation method includes but is not limited to assembling one or more pads having an active element area totaling more than one square foot adjacent a heat diffusion layer configured to support a patient; and causing primary control circuitry to implement a decision whether or not to cause the one or more heating elements to administer a therapeutically significant amount of power as thermal energy by passing current through the active element area totaling more than one square foot partly based on one or more thermal control sensors at the heat diffusion layer and partly based on an indication of a user preference and partly based on a compression-sensitive element indicating the patient being supported by the heat diffusion layer. In addition to the foregoing, other method aspects are described in the claims, drawings, and text forming a part of the disclosure set forth herein.

An embodiment provides a normothermia implementation system. In one variant, the normothermia implementation system includes but is not limited to one or more pads having an active element area totaling more than one square foot adjacent a heat diffusion layer configured to support a patient; and primary control circuitry configured to implement a decision whether or not to cause the one or more heating elements to administer a therapeutically significant amount of power as thermal energy by passing current through the active element area totaling more than one square foot partly based on one or more thermal control sensors at the heat diffusion layer and partly based on an indication of a user preference and partly based on a compression-sensitive element indicating the patient being supported by the heat diffusion layer.

In addition to the foregoing, various other method and/or system and/or program product aspects are set forth and described in the teachings such as text (e.g., claims and/or detailed description) and/or drawings of the present disclosure. The foregoing is a summary and thus may contain simplifications, generalizations, inclusions, and/or omissions of detail; consequently, those skilled in the art (professional or do-it-yourself deck builders, e.g.) will appreciate that the summary is illustrative only and is NOT intended to be in any way limiting. Other aspects, features, and advantages of the devices and/or processes and/or other subject matter described herein will become apparent by reference to the detailed description, the corresponding drawings, and/or in the teachings set forth herein.

BRIEF DESCRIPTION OF THE FIGURES

FIG. 1 depicts a portable system that facilitates support of and enhanced heat delivery to a patient pursuant to a medical procedure.

FIGS. 2-4 each depict a cross section of a pad comprising several layers.

FIG. 5 depicts an operating room implementing a patient support system configured to facilitate normothermia and other medically advantageous aspects.

FIGS. 6-7 each depict another view of a torso pad of FIG. 5.

FIG. 8 depicts event-sequencing logic (circuitry, e.g.) implementing components of systems described herein.

FIG. 9 depicts a fracture table with a sheet-type pad configured to support a prone patient.

FIG. 10 depicts a system for controlling heat delivery to a patient mounted onto a pole.

FIG. 12 depicts a connector suitable for use with pads as described herein.

FIG. 13 depicts a structure having several heating elements.

FIGS. 14-15 depict connectors suitable for use with heating or grounding elements described herein.

FIG. 16 depicts an assembly comprising one or more heating elements atop a foam base.

FIG. 17 depicts a system into which the assembly of FIG. 16 has been placed.

DETAILED DESCRIPTION

Figure 11:
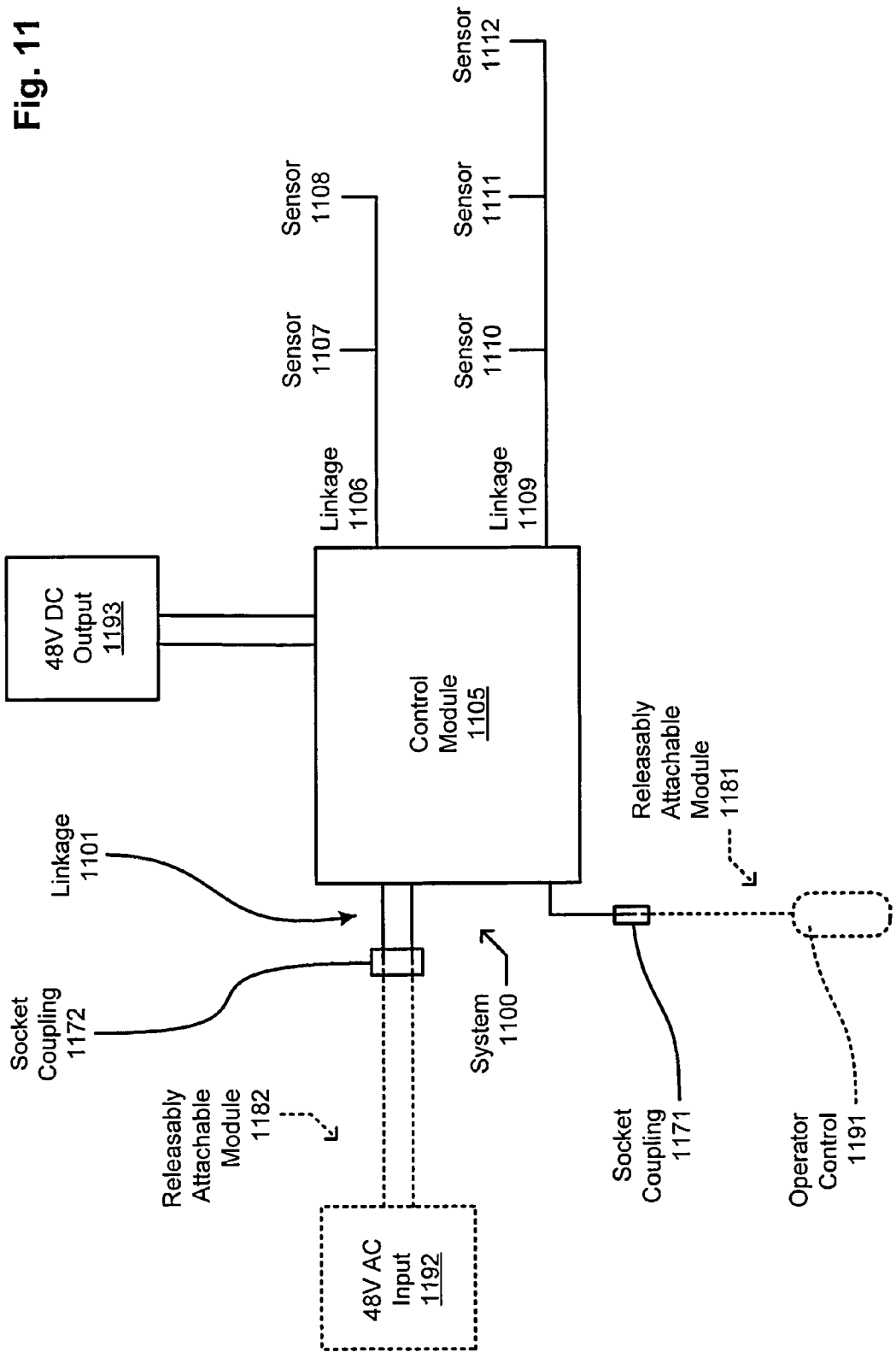
FIG. 11 depicts a normothermia implementation system schematically.

For a more complete understanding of embodiments, reference now is made to the following descriptions taken in connection with the accompanying drawings. The use of the same symbols in different drawings typically indicates similar or identical items, unless context dictates otherwise. The illustrative embodiments described in the detailed description, drawings, and claims are not meant to be limiting. Other embodiments may be utilized, and other changes may be made, without departing from the spirit or scope of the subject matter presented here.

In light of teachings herein, numerous existing techniques may be applied for implementing structural and control components as described herein without undue experimentation. See, e.g., U.S. Pat. No. 8,604,391 ("Heating blankets and pads"); U.S. Pat. No. 7,959,658 ("Heating system to alleviate hypothermia"); U.S. Pat. No. 7,666,215 ("System and method for determining and controlling core body temperature"); U.S. Pat. No. 7,196,289 ("Personal warming systems and apparatuses for use in hospitals and other settings, and associated methods of manufacture and use"); U.S. Pat. No. 7,176,419 ("Heating pad systems, such as for patient warming applications"); U.S. Pat. No. 6,582,456 ("Heated patient support apparatus"); U.S. Pat. No. 6,083,221 ("Resistive reusable electrosurgical return electrode"); U.S. Pat. No. 6,006,136 ("Heating pad"); U.S. Pat. No. 5,948,303 ("Temperature control for a bed"); U.S. Pat. No. 5,932,129 ("Thermal retention device"); U.S. Pat. No. 5,785,716 ("Temperature control pad for use during medical and surgical procedures"); U.S. Pat. No. 5,516,189 ("Portable heated seat"); U.S. Pat. No. 5,451,747 ("Flexible self-regulating heating pad combination and associated method"); U.S. Pat. No. 5,385,529 ("Method for controlling the temperature of an incubator"); U.S. Pat. No. 5,371,340 ("Low energy animal heating pad with directional heat transfer"); U.S. Pat. No. 5,324,911 ("Heated animal surgery table"); U.S. Pat. No. 5,138,138 ("Heating system for an operating table"); U.S. Pat. Pub. No. 2014/0018887 ("Thermotherapy device with detection of an obliquely positioned reclining surface"); U.S. Pat. Pub. No. 2013/0073012 ("Device and method for temperature management of heating pad systems"); U.S. Pat. Pub. No. 2012/0022620 ("Warming therapy device including heated mattress assembly"); U.S. Pat. Pub. No. 2011/0238143 ("System and method for altering and maintaining the body temperature of a patient"); U.S. Pat. Pub. No. 2011/0137388 ("Heating support for patients"); and U.S. Pat. Pub. No. 2008/0255641 ("Device and method for temperature management of heating pad systems").

With reference now to FIG. 1, a portable system 100 facilitates support of and enhanced heat delivery to a patient 150 pursuant to a medical procedure. System 100 includes a pad 187 supported by a frame 181 on wheels 188 and containing one or more heating elements 182 in a large conduction area configuration (having a total active element area larger than one square foot, e.g.) and a heat diffusion layer (see FIGS. 2-4) configured to support patient 150 (directly or otherwise) and to pass heat upward from the one or more heating elements 182 to the patient 150. System 100 also includes a retractable cord 189 (wound within spring-powered cord retraction reel 185 as shown, e.g.) treated with an antimicrobial coating at least partly supported by frame 181 and supporting an electrical plug 186 (a wall plug compatible with wall outlet 190, e.g.). System 100 also includes control circuitry 184 configured to decide whether or not to cause the one or more heating elements 182 to emit thermal energy at a substantial rate (more than 50 watts, e.g.) by passing current from the retractable cord 189 through (the active element area of) the heating element(s) 182 partly based on a first temperature sensor 171 at the heat diffusion layer and partly based on an indication of a user preference (a setting selected via a hand pendant 183 or a default value, e.g.). This can occur, for example, in a context in which adequate patient warming would otherwise require one or more caregivers 170 to pre-warm the pad 187 for several minutes and in which the system 100 is used at a facility with more than one wall outlet (in a hospital or nursing home, e.g.). Alternatively or additionally, system 100 may (optionally) also include a second temperature sensor 172 and one or more other sensors 173 as described below, each configured to provide a respective input to control circuitry 184.

Those skilled in the art will recognize that some list items may also function as other list items. Each such listed term should not be narrowed by any implication from other terms in the same list but should instead be understood in its broadest reasonable interpretation as understood by those skilled in the art.

"Active," "adjacent," "all," "any," "at," "atop," "automatic," "based," "battery-less," "between," "compressible," "conditional," "conductive," "configured," "coupled," "dielectric," "differing," "direct," "electrically," "first," "greater," "grounding," "having," "heated," "implementing," "indicating," "large," "lateral," "less," "life-threatening," "manifesting," "medial," "medical," "more," "on," "operator-selectable," "partly," "resistive," "retractable," "safety," "second," "significant," "substantial," "supported," "target," "therapeutic," "thermal," "thick," "through," "totaling," "upper," "within," or other such descriptors herein are used in their normal yes-or-no sense, not as terms of degree, unless context dictates otherwise. "To" is not used to articulate a mere intended purpose in phrases like "configured to," moreover, but is used normally, in descriptively identifying a particular device or pattern that is actually performing or implementing a task or arrangement or to a structure that can serve this function without significant modification. Positional relation terms like "along" or "adjacent" are used herein to refer to nominal (substantially ideal, e.g.) relations, having a difference or deviation of at most about 10° or 10% or 10 centimeters, unless context dictates otherwise.

With reference now to FIG. 2, there is shown a cross section of a pad 287 comprising several layers. A binding layer 243 (implemented as an adhesive or as a double-sided adhesive tape or as an electrically conductive foam, e.g.) secures a cover 246 to a large conduction area electrical grounding element 249 supported by a (nominally) nonconductive heat diffusion layer 245, an electric heating element 242, and an open-cell foam base 240 as shown. Heating element 242 and grounding element 249 may each be implemented as a carbon element or conductive fabric. Alternatively or additionally, cover 246 may be implemented as an electrically conductive black polymer foam or spray-on vinyl rendered conductive (having graphite microparticles therein to enhance electrical conductivity, e.g.). This can occur, for example, in a context in which pad 187 implements pad 287; in which an electrical current (for cauterization, e.g.) passing between the patient 150 and a ground terminal would otherwise create significant burning; and in which an annular portion of pad 287 (at the sides and bottom of pad 187, e.g.) is electrically nonconductive.

With reference now to FIG. 3, there is shown a cross section of a pad 387 comprising several layers. An electric heating element 342 is positioned between a heat diffusion layer 345 and an open-cell foam base 340 as shown. Each instance of heating element 342 may each be implemented as a carbon strip or conductive fabric, for example, as described below. A readily replaced waterproof sheet 344 is placed atop and adjacent diffusion layer, optionally as a component of a sleeve that is undersized so that foam base 340 is compressed during assembly. This can occur, for example, in a context in which an excessive gap 341 (sufficient to delay therapeutically significant conduction of heat to a patient 150 by more than a minute, e.g.) would otherwise exist between sheet 344 and diffusion layer 345.

With reference now to FIG. 4, there is shown a cross section of a pad 487 comprising several layers. Electric heating element 442 is positioned between a heat diffusion layer 445 and foam base 440 as shown. In some variants, one or both of foam base 440 and diffusion layer 445 are made of a closed-cell foam. One or more instances of sensor 475 (implementing various sensors described below, e.g.) are positioned at diffusion layer 445 (within or adjacent diffusion layer 445, e.g.). A smooth layer 448 (of waterproof washable vinyl or similar material, e.g.) covers diffusion layer 445 as shown. A textured layer 447 (configured to facilitate traction on or fixation to a frame 181, surgical table, or other supporting structure, e.g.) likewise supports foam base 440 (in a "sheet-type" implementation of pad 487 having a nominal thickness less than 5 centimeters, e.g.), well suited for use in surgical contexts of difficult patient positioning (on a fracture table, e.g.). See FIGS. 9 & 20.

With reference now to FIG. 5, there is shown an operating room 560 implementing a patient support system 500 configured to facilitate normothermia and other medically advantageous aspects described below. As shown, surgical table 564 includes a removable head pad 509, torso pad 505, and leg pad 510, one or more of which includes one or more heating elements 582 (instantiating heating element 242 or heating element 342, e.g.) in a large conduction area configuration as shown (effective to implement therapeutically significant normothermia during a surgery, e.g.). This can occur, for example, in a context in which therapeutically significant normothermia would otherwise cause an incapacitated patient 150, 950 to suffer serious complications (an elevated risk of infection or local burns, e.g.). System 500 also includes a control unit 504 (supported by mounting pole 542 as shown, e.g.) operably coupled with the heating element(s) 582 via a ribbon coupler 525. In some contexts, system 500 may also include one or more sensors (within torso pad 505, e.g.) transmitting signals (via cable 506, e.g.) to patient monitoring system 507. Alternatively or additionally, system 500 may include an electro-surgical generator operably coupled (via cable 563, e.g.) with a handheld cautery device 565 (via cable 563, e.g.) and with a grounding element 249 (wider than 12", e.g.) above at least a portion of the heating element(s) 582. This can occur, for example, in a context in which healthcare personnel would otherwise need to perform one or more additional setup protocols (positioning a grounding element in contact with at least 3% of the patient's skin, e.g.) to minimize burns resulting from current flow through the cautery device 565.

With reference now to FIG. 6, another view of the torso pad 505 of FIG. 5 is depicted. A nominal length 601 of torso pad 505 is depicted as being less than 60" and longer than 26". A nominal width 602 thereof is depicted as being less than 24" and more than 12". A nominal thickness 603 thereof is depicted as being less than 4" and more than 1". Several sensors 671, 672, 673, 674 are depicted as being within torso pad 505 (within or adjacent a heat diffusion layer 245, 345, 445 or grounding element 249, e.g.) as further described below with reference to FIG. 7.

With reference now to FIG. 7, another view of the torso pad 505 of FIG. 5 is depicted. As shown one or more sensors 672, 673 reside "in a longitudinally proximal majority" (at least including proximal half 701 of length 601, e.g.) of the pad. As shown one or more sensors 671, 672, 673, 674 reside "along a longitudinal edge" of the pad (not being within a medial half 702 of the width 602 of the pad, e.g.). Also as shown all of the sensors depicted reside "in the upper" half 703 of the thickness 603 of the pad (relative to a pad in a nominally horizontal position, e.g.). Moreover a lower surface (textured layer 447, e.g.) of the pad comprises a traction strip 777, optionally including Velcro®-like hooks configured to removably secure the pad to surgical table 564 or other such traction features (implementing textured layer 447, e.g.).

With reference now to FIG. 8, there is shown event-sequencing logic 800 (transistor-based circuitry and other electrical control components in a system described herein, e.g.). In some variants as depicted above, for example, systems described herein include power delivery circuitry 830 comprising one or more instances of values 801, 802 (as digital expressions, e.g.) used by control circuitry 831 or override circuitry 832 as described herein. Alternatively or additionally, such control may respond to one or more measurements 861, 862, 863 or thresholds 867, 868, 869 (in a machine-readable medium, e.g.).

With reference now to FIG. 9, there is shown a system 900 comprising a fracture table 964 including a sheet-type pad 987 (having a nominal thickness less than 5 centimeters, e.g.) configured to support a prone patient 950. In respective variants, for example, pad 987 may incorporate features from one or more pads 287, 387, 487 described above (implementing a grounding element 249 or gap 341 or textured layer 447, e.g.) such that a contiguous or other "large conduction" area 938 (one that totals more than one square foot, e.g.) is provided. A majority of area 938 is positioned adjacent patient 950 so that heat conducted (generally upward, e.g.) through a respective heat diffusion layer 245, 345, 445 of pad 987 is effectively administered to patient 950 without introducing turbulence into an operating room. Moreover in some variants a compressible material (foam, e.g.) is used as a diffusion layer 245, 345, 445 of pad 987, so that heat conduction is enhanced where patient 950 exerts weight, minimizing the emission of unproductive heat into the operating room.

With reference now to FIG. 10, there is shown an improved system for controlling heat delivery to a patient (before, during, or after medical or veterinary procedures, e.g.). The system includes a control unit 1004 (like that of FIG. 5, e.g.) positioned on a mounting pole (by tightening mounting knob 1041, e.g.) and operably coupled to one or more heating elements 182, 242, 342, 442, 582 (via a ribbon coupler 1025, e.g.) or other functional modules described herein (a patient monitoring system 507 or electro-surgical generator, e.g.). Control unit 1004 comprises one or more instances of standby/on toggles 1001, temperature selection buttons 1007, mode indicators 1008, or alarm toggles 1009 usable by an operator 1010. Standby/on toggle 1001, for example, permits operator 1010 to cause one or more event sequencing modules described herein (control circuitry 184, e.g.) to remain in a "standby" mode (in which at least one heating element 182, 242, 342, 442, 582 is unpowered but in which one or more sensors 171, 172, 173 at a heat diffusion layer 245, 345, 445 adjacent thereto are powered, e.g.). In some variants a "standby" mode is a default position of standby/on toggle 1001 (maintained there unless and until an operator 1010 activates another mode. In an "on" mode, for example, power delivery circuitry 830 passes current through at least one heating element 182, 242, 342, 442, 582 generally controlled as an automatic and conditional response to a thermal control sensor indicating a first temperature measurement 1061 differing from a target value 1071. This can occur, for example, in a context in which the thermal control and safety sensors are at (adjacent to or within, e.g.) a heat diffusion layer 245, 345, 445; in which mode indicators 1008 indicate a mode of standby/on toggle 1001 and of alarm toggle 1009 and of a selected nominal temperature (at any of 37° C. or 38° C., or 39° C. or 40° C., or 41° C. or 42° C., e.g.) selected by operator 1010 (by acquiescing to a default temperature or by pushing one or more temperature selection buttons 1007, e.g.).

With reference now to FIG. 11, there is shown an improved system 1100 for controlling heat delivery to a patient any of the above contexts. System 1100 includes a control module 1105 (implementing event-sequencing logic 800, e.g.) operably coupled via fixed linkage 1109 to one or more thermal control sensors 1110, 1111, 1112 (implementing primary temperature control, e.g.) and (via fixed linkage 1106) to one or more thermal safety sensors 1107, 1108 (implementing a thermal safety threshold 868, e.g.). Control module 1105 includes control circuitry 831 configured to pass a current through one or more heating elements described above (via 48-volt DC output 1193, e.g.) as an automatic and conditional response to a first temperature measurement 861 at a heat diffusion layer 245, 345, 445 (within or adjacent the diffusion layer, e.g.) differing from a target value 871 (set by default or by use of an operator control 1191 (using temperature selection buttons 1007 or a hand pendant 183, e.g.) in normal operation. Control module 1105 includes may also include override circuitry 832 configured to deactivate the heating element as an automatic and conditional response to a second temperature measurement 862 (via one or more thermal safety sensors 1107, 1108, e.g.) exceeding a thermal safety threshold 868 (just above a Curie point temperature 1968 of a sensor 1108 implemented as a switching-type positive temperature coefficient thermistor by at most 3° C., e.g.). As shown socket couplings 1171, 1172 are each likewise attached with a fixed linkage 1101 with control module 1105. As such 48-volt AC input 1192 is implemented as a releasably attachable module 1182 (using a quick-release coupling manufactured by LEMO®, e.g.) relative to control module 1105. Operator control 1191 is likewise implemented as a releasably attachable module 1181 (of a sliplock connector, e.g.) relative to control module 1105. This can occur, for example, in a context in which damage to a portion of system 1100 (a breakage of hand pendant 183 or a similar patient-accessible implementation of operator control 1191, e.g.) would otherwise render system 1100 inoperable for a therapeutically significant amount of time (hours, e.g.).

With reference now to FIG. 12, an improved system 1200 for controlling heat delivery to a patient in contexts like those of FIGS. 1-11. System 1200 includes a sub D connector 1212 operably coupled through a ribbon coupler 1225 to event-sequencing logic 800 configured to control electrical components of one or more pads 187, 287, 387, 487, 987 described herein (including one or more heating elements 242, 342, 442 or grounding elements 249, e.g.). As shown ribbon coupler 1225 includes shielded stranded wire 1221, 1222 (strands of woven copper wire, e.g.) along both edges thereof providing high-current pathways of power and ground, e.g.). Sub D connector 1212 may likewise be coupled to control circuitry (pendant 183 or control unit 504, e.g.) at an operator interface. This can occur, for example, in a context in which sub D connector 1212 has a large ground post 1232, 1233 at each end thereof and a power post 1231 therebetween; in which standard sensor pins 1241 thereof are configured to couple (electrically in respective pairs, e.g.) to temperature sensors 171, 671 described herein; in which safety sensor pins 1242 are configured to couple (electrically in respective pairs, e.g.) to temperature sensors 172, 672 described herein; and in which hot switching (by an inadvertent reversal of the ends of sub D connector when trying to insert sub D connector 1212 into control unit 504, e.g.) would otherwise ignite a flammable substance (in operating room 560, e.g.).

With reference now to FIG. 13, there is shown an improved system 1300 for controlling heat delivery to a patient in contexts like those described above. System 1300 includes two conductive bars 1330 (made of copper or a copper alloy, e.g.) each having a width 1340 of less than 2" (and optionally greater than 0.5", e.g.). Spanning between these bars 1330 are several resistive strips 1331 (primarily comprising carbon with a nominal width 1341 of at least 0.5", e.g.) with regular gaps 1332 (with a nominal width 1342 of at least 0.5") therebetween. Each such strip 1331 can thus comprise an instance of a heating element 242, 342, 442 (with the bars 1330 respectively at power and ground voltages, e.g.) or grounding element 249 (with at least one of the bars 1330 electrically coupled to a ground terminal of an electro-surgical generator, e.g.) as described above. Moreover system 1300 in the aggregate may implement either instance of "large factor" heating element(s) 182, 582 (having a total active element area totaling more one square foot, e.g.) as described above. This can occur, for example, in a context in which system 1300 includes at least 20 resistive strips 1331; in which each has a nominal active area of at least 8 square inches; in which each strip is somewhat shorter than (51% to 99% as long as, e.g.) a width 602 of a pad in which it resides; and in which such resistive structures (primarily comprising carbon, e.g.) would not otherwise provide a sufficiently reliable spread of thermal emission during a long-term use of the system 1300.

With reference now to FIG. 14, there is shown an improved system 1400 for delivering current through one or more heating or grounding elements (in a system 1300 like that of FIG. 13 comprising many resistive strips 1331 extending between conductive bars 1330, e.g.). System 1400 comprises a coupler 1425 like that of ribbon couplers 1025, 1225 (depicted above in FIGS. 10 & 12). Coupler 1425 abuts two high-current (braided or other) stranded wires 1420, 1430 (for power and ground of large conduction area heating elements described above, e.g.) which separate (at divergence 1436, e.g.) in a vicinity of the pad with which it engages. System 1400 also includes pairs of sensor coupling lines 1401, 1402 and a metal clamping connector 1427 for electrically coupling conductive bar 1330 to wire strands 1429 of a stranded wire 1420 that extend out beyond sleeve 1420.

With reference now to FIG. 15, there is shown an improved system 1500 for delivering current through one or more heating elements 182, 242, 342, 442, 582 or grounding elements 249 in an electrically resistive sheet configuration (comprising conductive fabric 1538, e.g.). Wire strands 1521 of a stranded wire 1520 (instantiating stranded wires 1221, 1222 described above, e.g.) extend beyond dielectric sleeve 1522 and engage a metal clamping connector 1527 electrically connected to a flat braid 1530 (of silver or a silver alloy, e.g.), providing a nominally uniform voltage (equal to that of power post 1231 or ground post 1233, e.g.) along the length of the flat braid 1530. Conductive thread 1577 provides numerous electrical connections along a plurality of rows of stitches 1572 (a straight stitch or zigzag stitch or chain stitch, e.g.) such that a nominally uniform voltage is formed along one edge as current flows through flat braid 1530 and fabric 1538. In some variants an overhang 1539 of the fabric may be folded over the flat braid 1530 so that a segment of the fabric 1538 is in direct contact with both sides of flat braid 1530 before stitching. This can occur, for example, in a context in which the use of fabric 1538 for heating or grounding in a pad 187, 287, 387, 487, 505, 509, 510, 987 described herein (trying to implement molten, adhesive, clamping, or other electrical connection technologies in lieu of stitching, e.g.) would otherwise create a dangerous and unpredictable circumstance in use by causing irregular heating (hotspots, e.g.) as the fabric 1538 flexes (when bearing a patient's weight, e.g.).

Figure 18:
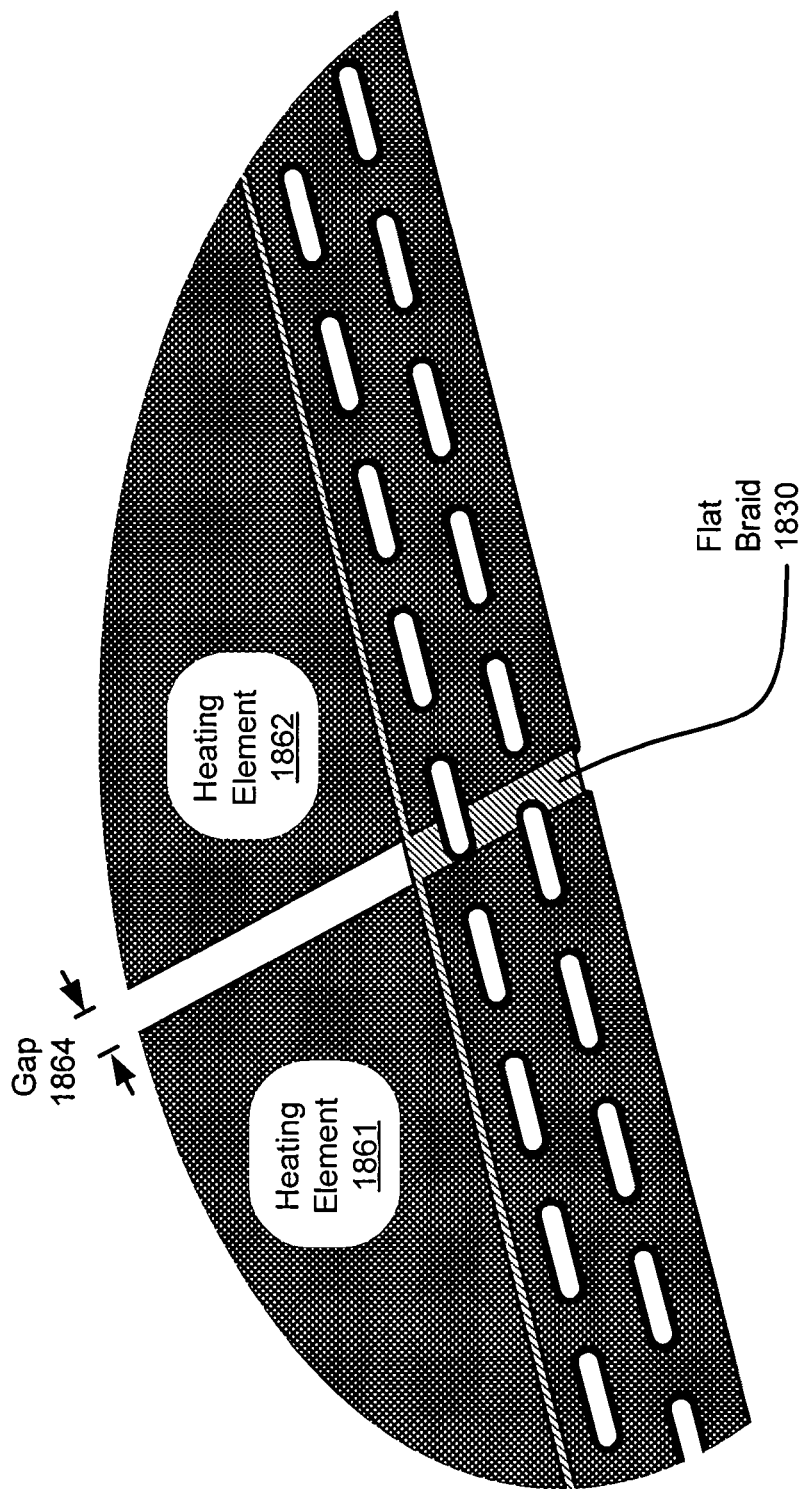
FIG. 18 depicts a gap between separated heating elements electrically coupled to a flat braid they share.

With reference now to FIG. 16, there is shown a context of one or more heating elements 1682 affixed atop foam base 1640 in a partially constructed configuration (with power and ground lines operable to pass current via control unit 1684 through the one or more heating elements 1682 not shown). With reference now to FIG. 17, there is shown a pad 1787 (inverted as shown) assembled by inserting foam base 1640 into a longitudinal opening 1762 of an undersized sleeve 1722 (creating a lateral and longitudinal compression of 1% to 4% of foam base 1640, e.g.) with the heating element(s) 1682 face down (opposite the water-resistant zipper pull tab 1761, e.g.). In some variants sleeve 1722 may include a Velcro®-type or other traction strip 1777 configured to engage a supporting surface (comprising frame 181, e.g.). Alternatively or additionally, in an instance in which system 1700 implements pad 287, the patient support surface pad 1787 (below the sleeve, in the inverted arrangement as shown) may include a conductive cover 246 electrically coupled (through a low-resistance binding layer 243, e.g.) to an instance of grounding element 249 therein. With reference now to FIG. 18, there is shown a gap 1864 between two separated heating elements 1861, 1862 electrically coupled to a flat braid 1830 they share (as an electrical ground, e.g.).

Figure 19:
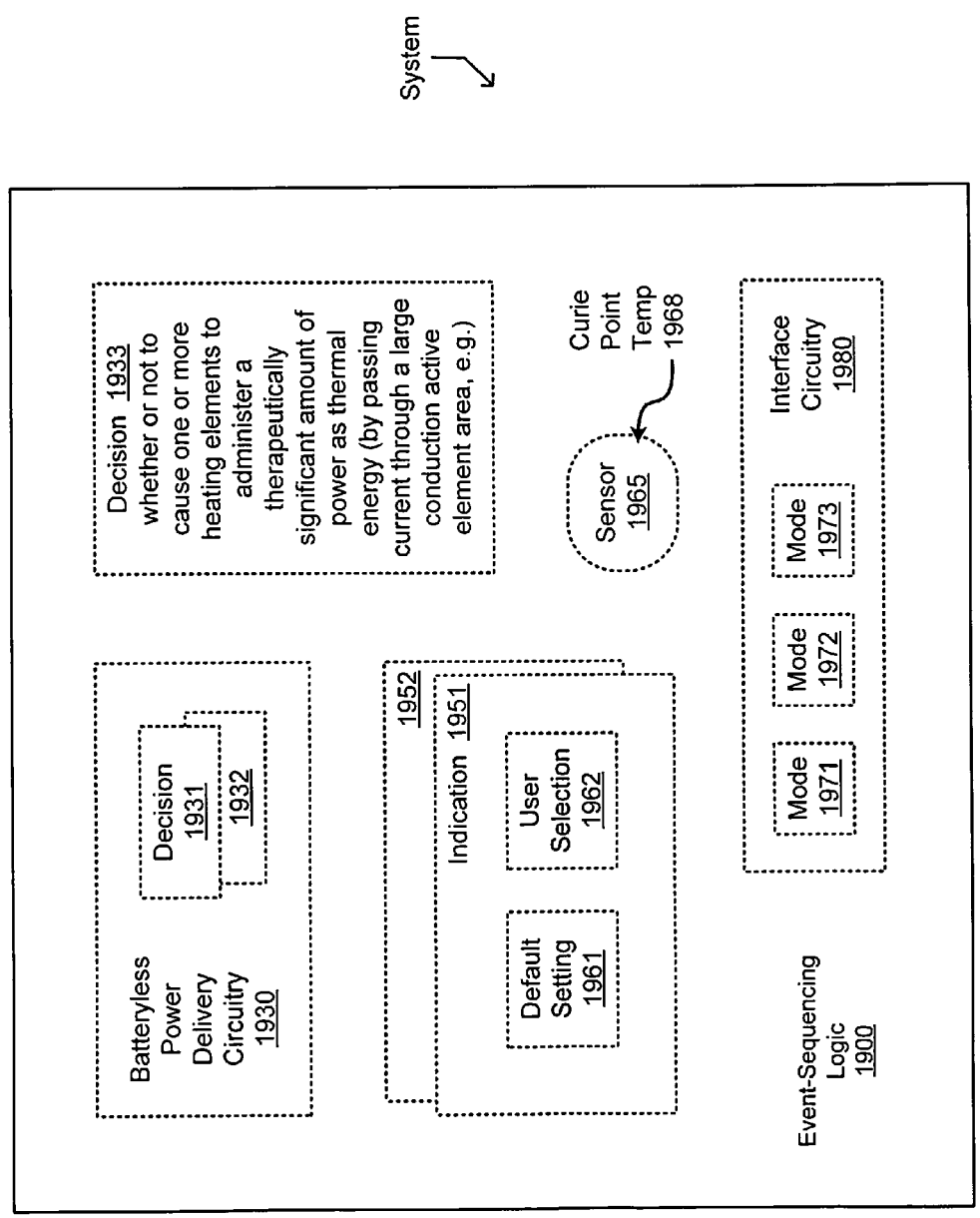
FIG. 19 depicts event-sequencing logic (circuitry, e.g.) implementing components of systems described herein.

With reference now to FIG. 19, there is shown event-sequencing logic 1900 (transistor-based circuitry and other electrical control components in a system described herein, e.g.), some of which may reside in pendant 183 or control circuitry 184 or adjacent a diffusion layer 245, 345, 445. In some variants as depicted above, for example, systems described herein include one or more instances of battery-less power delivery circuitry 1930 implementing one or more instances of decisions 1931, 1932, 1933 or measurements 861-863 described herein (as digital expressions, e.g.). A decision 1933 whether or not to cause one or more heating elements in a pad 187, 287, 387, 487, 505, 509, 510, 987, 1787 described herein to administer a therapeutically significant amount of power as thermal energy (by passing current through a large conduction active element area, e.g.) to a patient 150, 950 may depend upon which mode 1971, 1972, 1973 is indicated by control unit 1004 or other interface circuitry, for example. Such indications 1951, 1952 (of settings or modes apparently preferred by operator 1010, e.g.) may, for example, include one or more default settings 1961 or user selections 1962 described herein. Alternatively or additionally, one or more safety sensors described herein may be implemented as a posistor-type sensor 1965 with a Curie point temperature 1968 of approximately 40° C.

Figure 20:
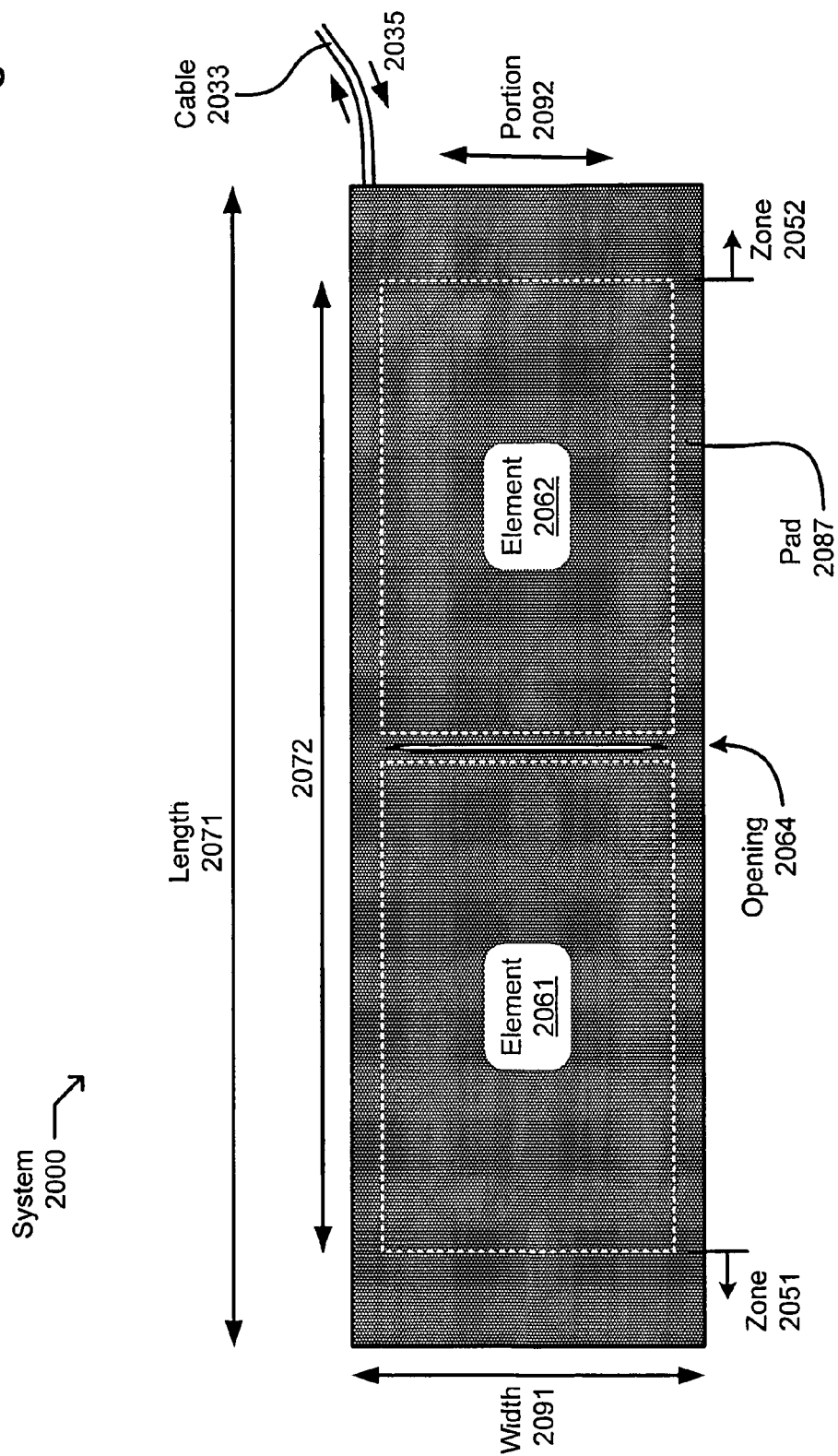
FIG. 20 depicts a system comprising a pad having an opening between separated heating elements.

With reference now to FIG. 20, there is shown a system 2000 comprising a cable 2033 operably coupled to a pad 2087 (instantiating one or more pads 187, 287, 387, 487, 987 described above, e.g.) in which respective separated heating elements 2061, 2062 (instantiating elements 1861, 1862, e.g.) are electrically coupled (adjacent a first lateral edge of pad 2087, e.g.) to a first instance of flat braid 1830 (electrically coupled to a first stranded wire 1520 of cable 2033, e.g.) and are electrically coupled (adjacent a second lateral edge of pad 2087, e.g.) on an opposite edge thereof to a second instance of flat braid 1830 (electrically coupled to a second stranded wire 1520 of cable 2033, e.g.) so that current 2035, when present, flows laterally across a medial portion 2092 of the width 2091 of pad 2087 (left-to-right relative to a prone patient thereon or front-to-back relative to a patient on her side on pad 2087, e.g.). Moreover the gap 1864 between elements 2061, 2062 facilitates a pass-through opening 2064 (large enough for a catheter or other conduit, e.g.) in a longitudinally centered portion 2072 of pad 2087. This can occur, for example, in a context in which pad 2087 implements a "sheet-type" implementation of pad having a nominal thickness less than 5 centimeters; in which none of the sensors described above are in either end-most zone 2051, 2052 or in medial portion 2092 of pad 2087; in which width 2091 is more than 12" and less than 40"; and in which a small healthcare facility (a rural clinic, e.g.) could not otherwise implement therapeutically significant warming to such a wide variety of medical or veterinary protocols.

Referring again to FIGS. 1-20, there are shown a variety of medical or veterinary patient support systems 100, 500, 900, 1100, 1200, 1300, 1400, 1500, 2000 and component structures thereof effective to facilitate therapeutically significant normothermia that is cost-effective for implementation in a healthcare facility or mobile emergency setting. In some contexts such systems may include a portable frame 181 supporting one or more pads 187, 287, 387, 487, 505, 987, 1787, 2087 containing one or more heating elements 182, 242, 342, 442, 1682, 1861, 1862, 2061, 2062 having an active element area 938, 1338 totaling more than one square foot adjacent a heat diffusion layer 245, 345, 445 configured to support a patient 150, 950; a retractable cord 189 supported by the portable frame 181 and including an electrical wall plug 186 configured to engage a wall outlet 190; and control circuitry 184 configured to decide whether or not to cause the one or more heating elements 182, 242, 342, 442, 1682, 1861, 1862, 2061, 2062 to radiate more than 10 watts thermally conducted to the patient by passing current 1235, 1335, 2035 from the retractable cord 189 supported by the portable frame 181 through the active element area 938, 1338 totaling more than one square foot adjacent the heat diffusion layer 245, 345, 445 configured to support the patient 150, 950. This can occur, for example, in a context in which the control circuitry 184 comprises battery-less power delivery circuitry 1930 configured to implement a decision 1931 whether or not to cause the one or more heating elements to radiate more than 50 watts of thermal energy (by passing current 1235, 1335, 2035 from the retractable cord supported by the portable frame through the active element area 938, 1338 totaling more than one square foot adjacent the heat diffusion layer 245, 345, 445 configured to support the patient, e.g.) partly based on a first temperature sensor 171, 1111 at the heat diffusion layer (indicating a first temperature measurement 861 differing from a target value 801, e.g.) and partly based on an indication 1951 of a user preference (a default setting 1961 or user selection 1962 manifested at a pendant 183, mounted control unit 504, or other operator control 1191, e.g.) and in which an implementation of therapeutically significant normothermia suitable for emergency response would otherwise require significant preheating (round-the-clock heating of the active element area or an emergency preparation period of several minutes, e.g.). Alternatively or additionally, each such heating element 182, 242, 342, 442, 1682, 1861, 1862, 2061, 2062 may be a substantially uniform material (a strip 1331 or sheet or fabric 1538 having a width and thickness that vary less than 10% along a direction of current flow therethrough, e.g.) electrically resistive enough so that at least 10% of the electrical power received by the support system (from wall outlet 190, e.g.) is converted into heat conducted to the patient thereby (radiated from the one or more heating elements through a heat diffusion layer, e.g.).

In another context such systems (e.g. implementing one or more systems 100, 800, 900, 1100, 1200, 1300, 1400, 1500, 2000) may include one or more pads 187, 287, 387, 487, 505, 987, 1787, 2087 having an active element area 938, 1338 totaling more than one square foot adjacent a heat diffusion layer 245, 345, 445 configured to physically support a patient 150, 950 (atop cover 246, sheet 344, or smooth layer 448, e.g.) and primary control circuitry 831 configured to implement a decision 1933 whether or not to cause the one or more heating elements 182, 242, 342, 442, 1682, 1861, 1862, 2061, 2062 to administer a therapeutically significant amount (more than 10 watts, e.g.) of power as thermal energy (administered to a medical patient 150, 950 or other subject via heat conduction primarily through a compressed portion of a heat diffusion layer 245, 345, 445 therebetween, e.g.) by passing current 1235, 1335, 2035 through the active element area 938, 1338 totaling more than one square foot partly based on one or more thermal control sensors 171, 671, 1111 at the heat diffusion layer 245, 345, 445 (responsive to an indication of a first temperature measurement 861 differing from a target value 801, e.g.) and partly based on an indication of a user preference (controlled by a patient 150, 950 or caregiver 170, e.g.) and partly based on a compression-sensitive element (a weight sensor 673 within a proximal half 701 of and within an upper half 703 of torso pad 505, e.g.) indicating the patient 150, 950 being physically supported by the heat diffusion layer 245, 345, 445 (indicating more than a threshold 869 of force exerted upon it, the threshold 869 corresponding to more than 0.5 lbs. and less than 5 lbs, e.g.).

In another context such systems may (optionally) include a heat diffusion layer 245, 345, 445; one or more large conduction area heating elements 182, 242, 342, 442, 582, 1682, 1861, 1862, 2061, 2062 adjacent the heat diffusion layer; one or more thermal control sensors 171, 671, 1111 configured to obtain a first temperature measurement 861 at the heat diffusion layer 245, 345, 445 (within or near the heat diffusion layer, e.g.); one or more thermal safety sensors 172, 672 configured to obtain a second temperature measurement 862 at the heat diffusion layer 245, 345, 445; override circuitry 832 operably coupled to the heating element adjacent the heat diffusion layer 245, 345, 445; interface circuitry 1980 configured to obtain an indication of a selected one (selected by default, e.g.) from a plurality of modes 1971, 1972, 1973 that includes at least a first operator-selectable mode (a "standby" mode 1971 of operation, e.g.) in which at least one thermal safety sensor of the one or more thermal safety sensors at the heat diffusion layer 245, 345, 445 is powered but in which the heating element adjacent the heat diffusion layer 245, 345, 445 is unpowered and that includes a second operator-selectable mode (an "active" mode 1972 of operation, e.g.) in which the one thermal safety sensor at the heat diffusion layer 245, 345, 445 is powered and in which the heating element adjacent the heat diffusion layer 245, 345, 445 is actively controlled; and primary control circuitry 831 configured to control the heating element adjacent the heat diffusion layer 245, 345, 445 as an automatic and conditional response to the one thermal control sensor at the heat diffusion layer 245, 345, 445 indicating a first temperature measurement differing from a target value if the second operator-selectable mode in which the one thermal safety sensor at the heat diffusion layer 245, 345, 445 is powered and in which the heating element adjacent the heat diffusion layer 245, 345, 445 is actively controlled is the selected one of the plurality unless the override circuitry 832 deactivates the heating element adjacent the heat diffusion layer 245, 345, 445 as an automatic and conditional response to (at least) the one thermal safety sensor 172, 672 (implemented by sensor 1965, e.g.) at the heat diffusion layer 245, 345, 445 indicating the second temperature measurement exceeding an effective thermal safety threshold 868 (e.g. within a few degrees greater than a Curie point temperature 1968 of the one thermal safety sensor at the heat diffusion layer 245, 345, 445). Such deactivation may include decoupling the primary control circuitry 831 from the heating element(s) 182, 242, 342, 442, 582, 1682, 1861, 1862, 2061, 2062 or may include activating a "standby" mode (in which the one thermal safety sensor 172, 672 at the heat diffusion layer 245, 345, 445 is powered but in which the heating element adjacent the heat diffusion layer 245, 345, 445 is unpowered, e.g.). This can occur, for example, in a context in which the Curie point temperature of the one thermal safety sensor 172, 672 (in respective embodiments) being about 38° C. (plus or minus 3° C., e.g.) and in which the thermal safety threshold is at most 42° C., whether or not the primary control circuitry controls the heating element adjacent the heat diffusion layer 245, 345, 445 as the automatic and conditional response to the one thermal control sensor 171, 671 at the heat diffusion layer 245, 345, 445 indicating the first temperature measurement 861 differing from the target value 801 being at least partly based on whether or not the first operator-selectable mode (in which the one thermal safety sensor at the heat diffusion layer 245, 345, 445 is powered but in which the heating element adjacent the heat diffusion layer 245, 345, 445 is unpowered, e.g.) is the selected one of the plurality.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B" in respective included configurations.

With respect to the numbered clauses and claims expressed below, all terms therein identify or describe one or more entities described above with particularity. With regard to methods described herein, those skilled in the art will appreciate that recited operations may generally be performed in any order, unless context dictates otherwise. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise. Also in the numbered clauses below, specific combinations of aspects and embodiments are articulated in a shorthand form such that (1) according to respective embodiments, for each instance in which a "component" or other such identifiers appear to be introduced (with "a" or "an," e.g.) more than once in a given chain of clauses, such designations may either identify the same entity or distinct entities; and (2) what might be called "dependent" clauses below may or may not incorporate, in respective embodiments, the features of "independent" clauses to which they refer or other features described above.

Clauses

1. A medical or veterinary patient support system configured to facilitate normothermia, comprising:
first means for supporting a patient 150, 950;
second means for heating the first means for supporting the patient as an automatic and conditional response to a first temperature measurement differing from a target value.

2. The patient support system of any of the above SYSTEM CLAUSES, further comprising:
a pad 287, 387, 487 that includes a heat diffusion layer and a first heating element and one or more thermal control sensors and one or more thermal safety sensors all at (within or adjacent, e.g.) the heat diffusion layer.

3. The patient support system of any of the above SYSTEM CLAUSES, further comprising:
a heat diffusion layer 245, 345, 445; and
control circuitry 184, 831 configured to control a first heating element adjacent the heat diffusion layer as an automatic and conditional response to at least one thermal control sensor at the heat diffusion layer indicating a first temperature measurement differing from a target value if an operator-selectable mode (an "on" mode, e.g.) in which the one thermal safety sensor at the heat diffusion layer is powered and in which the first heating element adjacent the heat diffusion layer is actively controlled is the selected one of the plurality comprising battery-less power delivery circuitry 1930 configured to implement therapeutically significant normothermia (delivering more than 10 watts via heat transfer structures as described herein, typically sufficient to improve the patient's chance of surviving a life-threatening emergency by at least 0.2%, e.g.) to the patient by delivering energy from a stationary outlet (wall outlet 190, e.g.) immediately to an electrically resistive active element area 938, 1338 totaling more than one square foot (comprising one or more heating elements that include the first heating element and have an aggregate resistance greater than 1 ohm and less than 1 kilohm, e.g.) adjacent the heat diffusion layer 245, 345, 445 configured to support the patient (atop cover 246, sheet 344, or smooth layer 448, e.g.).

4. The patient support system of any of the above SYSTEM CLAUSES, further comprising:
a heat diffusion layer 245, 345, 445; and
control circuitry 831 configured to control a first heating element 242, 342, 442 adjacent the heat diffusion layer as an automatic and conditional response partly based on a weight sensor 673 indicating the patient being supported by the heat diffusion layer and partly based on the first temperature measurement at the heat diffusion layer and partly based on an indication of a user preference (entered via control unit 504, e.g.).

5. The patient support system of any of the above SYSTEM CLAUSES, further comprising:
control circuitry 831 configured to control a first heating element adjacent a heat diffusion layer 245, 345, 445 as an automatic and conditional response partly based on the first temperature measurement at the heat diffusion layer and partly based on an indication of a user preference, the indication of the user preference manifesting a setting of a user interface having a default value less than 40° C. (at 37° C., e.g.).

6. The patient support system of any of the above SYSTEM CLAUSES, further comprising:
a pad 287, 387, 487 including a heat diffusion layer and an electrically conductive fabric 1538 and the one or more thermal control sensors and the one or more thermal safety sensors all adjacent the heat diffusion layer, the electrically conductive fabric 1538 adjacent the heat diffusion layer 245 comprising a grounding element 249 electrically coupled to a ground terminal of a cautery device 565 and to an electrically conductive cover 246 configured to be in direct contact with the patient (but not conductively coupled to a ground terminal of stranded wire 1222, e.g.).

7. The patient support system of any of the above SYSTEM CLAUSES, further comprising:
a pad 287, 387, 487 including a heat diffusion layer and an electrically conductive fabric and the one or more thermal control sensors and the one or more thermal safety sensors all adjacent the heat diffusion layer, the first heating element 1861 adjacent the heat diffusion layer comprising the electrically conductive fabric.

8. The patient support system of any of the above SYSTEM CLAUSES, further comprising:
a pad 287, 387, 487 including a heat diffusion layer and a multitude of electrically resistive strips 1331 and one or more thermal control sensors and one or more thermal safety sensors all adjacent the heat diffusion layer, the multitude of electrically resistive strips comprising the first heating element.

9. The patient support system of any of the above SYSTEM CLAUSES, further comprising:
a pad 287, 387, 487 including a heat diffusion layer and a first heating element adjacent the heat diffusion layer and one or more thermal control sensors and one or more thermal safety sensors, at least one of the one or more thermal control sensors configured to obtain the first temperature measurement at the heat diffusion layer in an upper half 703 of the pad and not in a medial half 702 of the pad.

10. The patient support system of any of the above SYSTEM CLAUSES, further comprising:
a pad 287, 387, 487 including a heat diffusion layer and a first heating element adjacent the heat diffusion layer and one or more thermal control sensors and one or more thermal safety sensors, at least one of the one or more thermal safety sensors configured to obtain a temperature measurement at the heat diffusion layer in an upper half of the pad and not in a medial half of the pad.

11. The patient support system of any of the above SYSTEM CLAUSES, further comprising:
a heat diffusion layer 245, 345, 445 thin enough and thermally conductive enough to conduct more than 10 watts of thermal energy from the active element area thereof totaling more than one square foot into a subject (a patient 150, 950 having an initial skin temperature of 35° C. or lower, e.g.) without burning any part of the subject (without elevating any part of the patient's skin to more than 42° C., e.g.).

12. The patient support system of any of the above SYSTEM CLAUSES, further comprising:
at least one heat diffusion layer 245, 345, 445;
one or more heating elements at the at least one heat diffusion layer and having an active element area thereof totaling more than one square foot, the one or more heating elements including a first heating element configured to conduct an average of more than 50 watts through the active element area totaling more than one square foot so that a therapeutically significant amount of thermal energy is conducted to the patient (effective for administering more than 10 watts of therapeutically significant active warming to the patient, e.g.) through the heat diffusion layer within a first minute of active warming.

13. The patient support system of any of the above SYSTEM CLAUSES, further comprising:
control circuitry 831 configured to generate a decision whether or not to pass current through an active element area 938, 1338 totaling more than one square foot partly based on an indication of a user preference and partly based on at least one thermal control sensor of the one or more thermal control sensors at a heat diffusion layer.

14. The patient support system of any of the above SYSTEM CLAUSES, further comprising:
a heat diffusion layer 245, 345, 445;
one or more heating elements 242, 342, 442 adjacent the heat diffusion layer and having an active element area totaling more than one square foot, the one or more heating elements including the first heating element; and
special-purpose circuitry configured to generate a decision whether or not to cause the active element area of the one or more heating elements (having an active element area) totaling more than one square foot to bear an electrical current from a retractable cord partly based on an indication of a user preference and partly based on at least one thermal control sensor of the one or more thermal control sensors at the heat diffusion layer.

15. The patient support system of any of the above SYSTEM CLAUSES, further comprising:
control circuitry (event-sequencing logic, e.g.) configured to implement a thermal safety threshold of at least one thermal safety sensor 1965 being in a positive temperature coefficient regime above a Curie point temperature 1968 of the one thermal safety sensor (by less than 10° C., e.g.).

16. The patient support system of any of the above SYSTEM CLAUSES, further comprising:

a pad 287, 387, 487 that includes a heat diffusion layer and a first heating element and one or more thermal control sensors and one or more thermal safety sensors all adjacent the heat diffusion layer, the pad having a nominal thickness less than 5 centimeters; and an operating table (surgical table 564, e.g.) configured to support the pad and the patient 150, 950 atop the pad.

17. The patient support system of any of the above SYSTEM CLAUSES, further comprising:

a pad 987 that includes a heat diffusion layer and a first heating element and one or more thermal control sensors and one or more thermal safety sensors all adjacent the heat diffusion layer, the pad having a nominal thickness less than 5 centimeters; and an operating table configured to support the pad and the patient 950 atop the pad, the operating table being a fracture table.

18. The patient support system of any of the above SYSTEM CLAUSES, further comprising:

a pad 287, 387, 487 that includes a heat diffusion layer and a first heating element and one or more thermal control sensors and one or more thermal safety sensors all adjacent the heat diffusion layer;

a portable frame that supports the pad; and a handheld device (pendant 183, e.g.) including interface circuitry configured to indicate a selected one from a plurality of modes that includes at least a first operator-selectable mode (a "standby" mode, e.g.) in which at least one thermal safety sensor of the one or more thermal safety sensors at the heat diffusion layer is powered but in which the first heating element adjacent the heat diffusion layer is unpowered and that includes a second operator-selectable mode (an "active" mode, e.g.) in which the one thermal safety sensor at the heat diffusion layer is powered and in which the first heating element adjacent the heat diffusion layer is actively controlled.

19. The patient support system of any of the above SYSTEM CLAUSES, further comprising:

an operating table including a pad (torso pad 505, e.g.) that includes a heat diffusion layer and a first heating element 582 adjacent the heat diffusion layer and one or more thermal control sensors and one or more thermal safety sensors; and a mounting pole 542 configured to support the interface circuitry configured to indicate a selected one from a plurality of modes that includes at least a first operator-selectable mode in which at least one thermal safety sensor of the one or more thermal safety sensors at the heat diffusion layer is powered but in which the first heating element 242, 342, 442, 582 is unpowered and that includes the second operator-selectable mode in which the one thermal safety sensor at the heat diffusion layer is powered and in which the first heating element is actively controlled.

20. The patient support system of any of the above SYSTEM CLAUSES, further comprising:

a pad 387 including a sheet 344 comprising a vinyl-containing fabric.

21. The patient support system of any of the above SYSTEM CLAUSES, further comprising:

a pad 287, 387, 487 having a length greater than 20" and a width greater than 10", a first heating element spanning between a power conduit and a ground conduit, the power conduit and the ground conduit each extending longitudinally along a substantial portion 2072 (at least half, e.g.) of the length 601, 2071 of the pad.

22. The patient support system of any of the above SYSTEM CLAUSES, further comprising:

a pad 287, 387, 487 having a length 2071 less than 7' and a width 2091 less than 30", the first heating element configured to carry electrical current 1235, 1335 laterally across a substantial portion 2092 of the width 2091 of the pad.

23. The patient support system of any of the above SYSTEM CLAUSES, further comprising:

a heat diffusion layer 245, 345, 445 comprising a compressible foam (an open cell foam 2-5 millimeters thick, e.g.).

24. The patient support system of any of the above SYSTEM CLAUSES, further comprising:

a heat diffusion layer 245, 345, 445 comprising a dielectric fabric (a medium weight felt wool, e.g.).

25. The patient support system of any of the above SYSTEM CLAUSES, further comprising:

a frame 181;

a retractable cord 189 supported by the frame;

one or more heating elements 1682, 1862 adjacent a heat diffusion layer 245, 345, 445 and having an active element area totaling more than one square foot, the one or more heating elements including a first heating element; and special-purpose circuitry configured to generate a decision 1932 whether or not to cause the active element area of the one or more heating elements totaling more than one square foot to bear an electrical current from the retractable cord partly based on an indication 1952 of a user preference and partly based on at least one thermal control sensor at the heat diffusion layer and partly based on at least one thermal safety sensor at the heat diffusion layer.

26. The patient support system of any of the above SYSTEM CLAUSES, further comprising:

interface circuitry 1980 configured to manifest an indication of a user preference implementing a target temperature greater than 35° C.

27. The patient support system of any of the above SYSTEM CLAUSES, further comprising:

interface circuitry 1980 configured to manifest an indication of a user preference implementing a target temperature less than 42° C.

28. The patient support system of any of the above SYSTEM CLAUSES, further comprising:

a frame 181;

a pad 187 including a heat diffusion layer and one or more heating elements and one or more thermal control sensors and one or more thermal safety sensors all adjacent the heat diffusion layer; and a retractable cord 189 at least partly wound within a retractable cord reel 185 mounted onto the frame 181 and supporting an electrical plug operably coupled to control circuitry configured to generate one or more decisions 1931, 1932, 1933.

29. The patient support system of any of the above SYSTEM CLAUSES, further comprising:

a frame 181 configured to support the patient 150; and a plurality of wheels 188 configured to support the frame.

30. The patient support system of any of the above SYSTEM CLAUSES, further comprising:

control circuitry 184 configured to decide whether or not to cause the one or more heating elements 182 to emit thermal energy at a substantial rate (more than 50 watts, e.g.) by passing current from a retractable cord 189 through (the active element area of) the heating element(s) 182 partly based on a first temperature sensor 171 at the heat diffusion layer and partly based on an indication of a user preference.

All of the patents and other publications referred to above (not including websites) are incorporated herein by reference generally—including those identified in relation to particular new applications of existing techniques—to the extent not inconsistent herewith. While various system, method, article of manufacture, or other embodiments or aspects have been disclosed above, also, other combinations of embodiments or aspects will be apparent to those skilled in the art in view of the above disclosure. The various embodiments and aspects disclosed above are for purposes of illustration and are not intended to be limiting, with the true scope and spirit being indicated in the final claim set that follows.

What is claimed is:

1. A cost-effective medical or veterinary patient support system configured to facilitate normothermia, comprising:
a heat diffusion layer;
a first heating element at the heat diffusion layer;
one or more thermal control sensors configured to obtain a first temperature measurement at the heat diffusion layer;
one or more thermal safety sensors configured to obtain a second temperature measurement at the heat diffusion layer;
override circuitry operably coupled to the first heating element at the heat diffusion layer;
interface circuitry configured to indicate a selected one from a plurality of modes that includes at least a first operator-selectable mode in which at least one thermal safety sensor of the one or more thermal safety sensors at the heat diffusion layer is powered but in which the first heating element at the heat diffusion layer is unpowered and that includes a second operator-selectable mode in which the one thermal safety sensor at the heat diffusion layer is powered and in which the first heating element at the heat diffusion layer is actively controlled; and
primary control circuitry configured to control the first heating element at the heat diffusion layer as an automatic and conditional response to the one thermal control sensor at the heat diffusion layer indicating a first temperature measurement differing from a target value if the second operator-selectable mode in which the one thermal safety sensor at the heat diffusion layer is powered and in which the first heating element at the heat diffusion layer is actively controlled is the selected one of the plurality unless the override circuitry deactivates the first heating element at the heat diffusion layer as an automatic and conditional response to the one thermal safety sensor at the heat diffusion layer indicating the second temperature measurement exceeding a thermal safety threshold, whether or not the primary control circuitry controls the first heating element at the heat diffusion layer as the automatic and conditional response to the first temperature sensor at the heat diffusion layer indicating the first temperature measurement differing from the target value being at least partly based on whether or not the first operator-selectable mode in which the one thermal safety sensor at the heat diffusion layer is powered but in which the first heating element at the heat diffusion layer is unpowered is the selected one of the plurality.

2. The patient support system of claim 1, further comprising:
a frame supported by a plurality of wheels and configured to support the patient; and
the primary control circuitry configured to control the first heating element at the heat diffusion layer as the automatic and conditional response to the one thermal control sensor at the heat diffusion layer indicating a first temperature measurement differing from the target value if the second operator-selectable mode in which the one thermal safety sensor at the heat diffusion layer is powered and in which the first heating element at the heat diffusion layer is actively controlled is the selected one of the plurality comprising battery-less power delivery circuitry configured to implement therapeutically significant normothermia to the patient by delivering energy from a stationary outlet immediately to an electrically resistive active element area totaling more than one square foot at the heat diffusion layer configured to support a patient.

3. The patient support system of claim 1, further comprising:
a pad including the heat diffusion layer and an electrically conductive fabric and the one or more thermal control sensors and the one or more thermal safety sensors all at the heat diffusion layer, the first heating element at the heat diffusion layer comprising the electrically conductive fabric, at least one of the one or more thermal control sensors configured to obtain the first temperature measurement at the heat diffusion layer in an upper half of the pad and not in a medial half of the pad.

4. The patient support system of claim 1, further comprising:
the control circuitry configured to generate a decision whether or not to pass current through an active element area totaling more than the one square foot partly based on an indication of a user preference and partly based on at least one thermal control sensor of the one or more thermal control sensors at the heat diffusion layer.

5. The patient support system of claim 1, further comprising:
a pad that includes the heat diffusion layer and the first heating element and the one or more thermal control sensors and the one or more thermal safety sensors all adjacent the heat diffusion layer, the pad having a nominal thickness less than 5 centimeters and configured to implement active warming upon a patient atop the pad; and
a fracture table configured to support the pad and the patient atop the pad.

6. The patient support system of claim 1, further comprising:
one or more heating elements at the heat diffusion layer and having an active element area totaling more than one square foot, the one or more heating elements including the first heating element; and
special-purpose circuitry configured to generate a decision whether or not to cause the active element area of the one or more heating elements totaling more than one square foot to bear an electrical current from a retractable cord partly based on an indication of a user preference and partly based on at least one thermal control sensor of the one or more thermal control sensors at the heat diffusion layer.

7. The patient support system of claim 1, further comprising:
the thermal safety threshold of at least one thermal safety sensor of the one or more thermal safety sensors being in a positive temperature coefficient regime above a Curie point temperature of the one thermal safety sensor.

8. The patient support system of claim 1, further comprising:

a pad that includes the heat diffusion layer and the first heating element and the one or more thermal control sensors and the one or more thermal safety sensors all at the heat diffusion layer, the pad having a nominal thickness less than 5 centimeters; and an operating table configured to support the pad and the patient atop the pad.

9. The patient support system of claim 1, further comprising:

a pad that includes the heat diffusion layer and the first heating element and the one or more thermal control sensors and the one or more thermal safety sensors all at the heat diffusion layer;

a portable frame that supports the pad; and a handheld device including the interface circuitry configured to indicate the selected one from the plurality of modes that includes at least the first operator-selectable mode in which at least one thermal safety sensor of the one or more thermal safety sensors at the heat diffusion layer is powered but in which the first heating element at the heat diffusion layer is unpowered and that includes the second operator-selectable mode in which the one thermal safety sensor at the heat diffusion layer is powered and in which the first heating element at the heat diffusion layer is actively controlled.

10. The patient support system of claim 1, further comprising:

a pad that includes the heat diffusion layer and the first heating element and the one or more thermal control sensors and the one or more thermal safety sensors all at the heat diffusion layer, the pad having a length greater than 20" and less than 7' and a width greater than 10" and less than 2', the first heating element spanning between a power conduit and a ground conduit, the power conduit and the ground conduit each extending longitudinally along at least half of the length of the pad, the first heating element configured to carry electrical current laterally across at least half of the width of the pad.

11. The patient support system of claim 1, further comprising:

one or more heating elements at the heat diffusion layer and having an active element area totaling more than one square foot, the one or more heating elements including the first heating element; and special-purpose circuitry configured to generate a decision whether or not to cause the active element area of the one or more heating elements totaling more than one square foot to bear an electrical current from a retractable cord partly based on an indication of a user preference and partly based on at least one thermal control sensor of the one or more thermal control sensors at the heat diffusion layer and partly based on at least one thermal safety sensor of the one or more thermal safety sensors at the heat diffusion layer.

12. The patient support system of claim 1, further comprising:

the interface circuitry configured to manifest an indication of a user preference implementing a target temperature greater than 35° C. and less than 42° C.; and a pad including the heat diffusion layer and an electrically conductive fabric and the one or more thermal control sensors and the one or more thermal safety sensors and one or more heating elements having an active element area totaling more than the one square foot all at the heat diffusion layer, the one or more heating elements having an active element area totaling more than the one square foot including the first heating element.

13. The patient support system of claim 1, further comprising:

a frame;

a pad including the heat diffusion layer and the one or more heating elements and the one or more thermal control sensors and the one or more thermal safety sensors all at the heat diffusion layer; and a retractable cord at least partly wound within a retractable cord reel mounted onto the frame and supporting an electrical plug operably coupled to the primary control circuitry configured to control the first heating element at the heat diffusion layer as the automatic and conditional response to the one thermal control sensor at the heat diffusion layer indicating the first temperature measurement differing from the target value if the second operator-selectable mode in which the one thermal safety sensor at the heat diffusion layer is powered and in which the first heating element at the heat diffusion layer is actively controlled is the selected one of the plurality unless the override circuitry deactivates the first heating element at the heat diffusion layer as the automatic and conditional response to the one thermal safety sensor at the heat diffusion layer indicating the second temperature measurement exceeding the thermal safety threshold, whether or not the primary control circuitry controls the first heating element at the heat diffusion layer as the automatic and conditional response to the first temperature sensor at the heat diffusion layer indicating the first temperature measurement differing from the target value being at least partly based on whether or not the first operator-selectable mode in which the one thermal safety sensor at the heat diffusion layer is powered but in which the first heating element at the heat diffusion layer is unpowered is the selected one of the plurality.

* * * * *